United States Patent
Marin et al.

(10) Patent No.: US 11,421,056 B2
(45) Date of Patent: Aug. 23, 2022

(54) POLYOLEFIN POLYMER COMPOSITION

(71) Applicant: W.R. Grace & Co.-Conn., Columbia, MD (US)

(72) Inventors: Vladimir P. Marin, Pasadena, TX (US); Jan Van Egmond, Charleston, WV (US); Ahmed Hintolay, Pasadena, TX (US)

(73) Assignee: W.R. GRACE & CO.-CONN., Columbia, MD (US)

( * ) Notice: Subject to any disclaimer, the term of this patent is extended or adjusted under 35 U.S.C. 154(b) by 0 days.

(21) Appl. No.: 16/762,353

(22) PCT Filed: Nov. 13, 2018

(86) PCT No.: PCT/US2018/060768
§ 371 (c)(1),
(2) Date: May 7, 2020

(87) PCT Pub. No.: WO2019/094942
PCT Pub. Date: May 16, 2019

(65) Prior Publication Data
US 2020/0270381 A1    Aug. 27, 2020

Related U.S. Application Data

(60) Provisional application No. 62/585,137, filed on Nov. 13, 2017.

(51) Int. Cl.
| | | |
|---|---|---|
| C08F 210/16 | (2006.01) | |
| C08L 23/16 | (2006.01) | |
| C08F 210/06 | (2006.01) | |
| C07C 69/78 | (2006.01) | |
| C08F 110/06 | (2006.01) | |
| C08F 4/618 | (2006.01) | |
| C08F 4/654 | (2006.01) | |
| C08F 4/656 | (2006.01) | |
| B01J 31/02 | (2006.01) | |
| C08F 4/649 | (2006.01) | |
| B01J 31/36 | (2006.01) | |

(52) U.S. Cl.
CPC ............ *C08F 210/06* (2013.01); *C07C 69/78* (2013.01); *C08F 110/06* (2013.01); *C08F 210/16* (2013.01); *C08L 23/16* (2013.01); *B01J 31/0258* (2013.01); *B01J 31/36* (2013.01); *C08F 4/6183* (2013.01); *C08F 4/6186* (2013.01); *C08F 4/6497* (2013.01); *C08F 4/656* (2013.01); *C08F 4/6543* (2013.01); *C08F 4/6565* (2013.01); *C08F 2410/03* (2013.01); *C08F 2500/12* (2013.01); *C08F 2500/18* (2013.01); *C08F 2500/24* (2013.01); *C08F 2800/20* (2013.01); *C08L 2207/02* (2013.01)

(58) Field of Classification Search
CPC .. C08F 210/06; C08F 110/06; C08F 2410/03; C08F 2500/24; C08F 2800/20; C07C 69/78; C08L 23/16; C08L 23/14; C08L 2207/02; C08L 2314/02; C08L 2500/12; C08L 2500/18
USPC ........................................................ 428/402
See application file for complete search history.

(56) References Cited

U.S. PATENT DOCUMENTS

| | | |
|---|---|---|
| 4,784,983 A | 11/1988 | Mao et al. |
| 4,861,847 A | 8/1989 | Mao et al. |
| 5,767,034 A | 6/1998 | Diaz-Barrios et al. |
| 6,376,417 B1 | 4/2002 | Yang et al. |
| 6,469,112 B2 | 10/2002 | Cheng et al. |
| H2060 H | 3/2003 | Spencer et al. |
| 6,683,017 B2 | 1/2004 | Gao et al. |
| 6,703,339 B2 | 3/2004 | Li et al. |
| 7,196,140 B2 | 3/2007 | Dahn et al. |
| 7,332,455 B2 | 2/2008 | Wei et al. |
| 7,351,778 B2 | 4/2008 | Gao et al. |

(Continued)

FOREIGN PATENT DOCUMENTS

| | | |
|---|---|---|
| CN | 101724105 A | 6/2010 |
| CN | 105622789 A | 6/2016 |

(Continued)

OTHER PUBLICATIONS

International Search Report Corresponding to Application No. PCT/US2018/057980 dated Jan. 15, 2019.
International Search Report Corresponding to Application No. PCT/US2018/059311 dated Jan. 16, 2019.
International Search Report Corresponding to Application No. PCT/US2018/060768 dated Mar. 18, 2019.
European Search Report on EP 18875540.9 dated Oct. 20, 2021.

(Continued)

*Primary Examiner* — Rip A Lee
(74) *Attorney, Agent, or Firm* — Foley & Lardner LLP

(57) ABSTRACT

The present disclosure is generally directed to polyolefin polymers, such as polypropylene homopolymers, and propylene-ethylene copolymers that have improved flow properties. In one embodiment, the polymers can be produced using a solid catalyst component that includes a) dissolving a halide-containing magnesium compound in a mixture, the mixture including an epoxy compound, an organic phosphorus compound, and a hydrocarbon solvent to form a homogenous solution; b) treating the homogenous solution with an organosilicon compound during or after the dissolving step; c) treating the homogenous solution with a first titanium compound in the presence of a first non-phthalate electron donor, and an organosilicon compound, to form a solid precipitate; and d) treating the solid precipitate with a second titanium compound in the presence of a second non-phthalate electron donor to form the solid catalyst component, where the process is free of carboxylic acids and anhydrides.

18 Claims, 7 Drawing Sheets

(56) References Cited

U.S. PATENT DOCUMENTS

| | | | |
|---|---|---|---|
| 7,388,060 B2 | 6/2008 | Wang et al. | |
| 7,893,003 B2* | 2/2011 | Chen | C08F 10/06 |
| | | | 502/158 |
| 8,003,558 B2 | 8/2011 | Chang | |
| 8,067,510 B2* | 11/2011 | Sheard | C08F 10/06 |
| | | | 526/348 |
| 8,211,819 B2 | 7/2012 | Chang | |
| 8,227,370 B2 | 7/2012 | Chang | |
| 8,318,626 B2 | 11/2012 | Chang | |
| 8,765,626 B2 | 7/2014 | Chang | |
| 8,778,826 B2 | 7/2014 | Gonzalez et al. | |
| 8,779,058 B2* | 7/2014 | Sheard | C08F 10/02 |
| | | | 525/240 |
| 8,822,602 B2* | 9/2014 | Leskinen | C08L 23/12 |
| | | | 525/240 |
| 8,841,390 B2* | 9/2014 | Leskinen | C08L 51/06 |
| | | | 524/451 |
| 8,933,180 B2 | 1/2015 | Chang | |
| 9,593,182 B2 | 3/2017 | Marin et al. | |
| 9,637,575 B2 | 5/2017 | Nguyen et al. | |
| 9,663,595 B2 | 5/2017 | Nguyen et al. | |
| 9,663,647 B2* | 5/2017 | Van Egmond | C08L 23/12 |
| 9,714,302 B2 | 7/2017 | Umezawa-Vizzini et al. | |
| 9,738,736 B2 | 8/2017 | Marin et al. | |
| 9,751,960 B2 | 9/2017 | Li et al. | |
| 9,890,274 B2* | 2/2018 | Wang | C08L 23/12 |
| 10,059,784 B2* | 8/2018 | Van Egmond | C08F 210/06 |
| 10,208,146 B2 | 2/2019 | Wang et al. | |
| 10,358,505 B2* | 7/2019 | Chen | C08F 4/16 |
| 10,526,427 B2 | 1/2020 | Fukuda et al. | |
| 10,662,267 B2* | 5/2020 | Nguyen | B01J 31/26 |
| 10,759,931 B2* | 9/2020 | Kniesel | C08L 23/20 |
| 2002/0169072 A1 | 11/2002 | Nakayama et al. | |
| 2009/0171044 A1 | 7/2009 | Spencer | |
| 2010/0240836 A1 | 9/2010 | Denifl et al. | |
| 2010/0249330 A1* | 9/2010 | Massari | C08F 210/06 |
| | | | 525/240 |
| 2012/0004378 A1* | 1/2012 | Hosaka | C08F 10/06 |
| | | | 502/124 |
| 2013/0102744 A1 | 4/2013 | Fushimi et al. | |
| 2013/0261273 A1* | 10/2013 | Chen | C08F 4/16 |
| | | | 526/194 |
| 2013/0296510 A1 | 11/2013 | Guo et al. | |
| 2015/0099842 A1* | 4/2015 | Gahleitner | C08L 23/06 |
| | | | 524/451 |
| 2016/0102156 A1 | 4/2016 | Umezawa-Vizzini et al. | |
| 2016/0289436 A1 | 10/2016 | Van Egmond et al. | |
| 2016/0297906 A1 | 10/2016 | Van Egmond | |
| 2017/0009068 A1* | 1/2017 | Kahlen | C08F 210/06 |
| 2017/0096503 A1* | 4/2017 | Marin | C08F 110/06 |
| 2017/0313865 A1* | 11/2017 | Wang | C08L 23/16 |

FOREIGN PATENT DOCUMENTS

| | | |
|---|---|---|
| RU | 2265614 C2 | 12/2005 |
| RU | 2502746 C2 | 12/2013 |
| RU | 2527036 C2 | 8/2014 |
| RU | 2528384 C2 | 9/2014 |
| RU | 2532543 C2 | 11/2014 |
| WO | WO2012/062734 A1 | 5/2012 |
| WO | WO2012/088028 A1 | 6/2012 |
| WO | WO-2015/185490 A1 | 12/2015 |

OTHER PUBLICATIONS

Communication pursuant to Rule 164(1) EPC re Partial Supplementary European Search Report on EP 18875540.9 dated Oct. 20, 2021 (7 pages).

Extended European Search Report on EP Application 18876554.9 dated Oct. 28, 2021 (4 pages).

First Examination Report on IN Application 202017019820 dated Nov. 16, 2021 (5 pages) (English translation included).

First Examination Report on IN Application No. 202017019815 dated Nov. 26, 2021 (8 pages) (English translation included).

International Preliminary Report on Patentability on PCT/US2018/057980 dated May 19, 2020 (7 pages).

International Preliminary Report on Patentability on PCT/US2018/059311 dated May 19, 2020 (7 pages).

International Preliminary Report on Patentability on PCT/US2018/060768 dated May 19, 2020 (6 pages).

Office Action and Search Report from RU 2020119468 dated Feb. 10, 2022, 31 pages.

Office Action and Search Report on RU Application No. 2020119397 dated Mar. 23, 2022 (English translation included, 29 pages).

* cited by examiner

POLYOLEFIN POLYMER COMPOSITION

CROSS REFERENCE TO RELATED APPLICATIONS

This application is the U.S. National Stage entry and claims priority to International Application Number PCT/US2018/060768 filed under the Patent Cooperation Treaty and having a filing date of Nov. 13, 2018, which claims priority to U.S. Provisional Application No. 62/585,137 having a filing date of Nov. 13, 2017, all of which are hereby incorporated by reference herein in their entirety for all purposes.

BACKGROUND

Polyolefins are a class of polymers derived from simple olefins. Known methods of making polyolefins involve the use of Ziegler-Natta polymerization catalysts. These catalysts polymerize olefin monomers using a transition metal halide to provide a polymer with various types of stereochemical configurations.

One type of Ziegler-Natta catalyst system comprises a solid catalyst component, constituted by a magnesium halide on which are supported a titanium compound and an internal electron donor compound. In order to maintain high selectivity for an isotactic polymer product, internal electron donor compounds can be added during catalyst synthesis. The internal donor can be of various types. Conventionally, when a higher crystallinity of the polymer is required, an external donor compound is also added during the polymerization reaction.

During the past 30 years, numerous supported Ziegler-Natta catalysts have been developed which afford a much higher activity in olefin polymerization reactions and much higher content of crystalline isotactic fractions in the polymers they produce. With the development of internal and external electron donor compounds, polyolefin catalyst systems are continuously renovated.

Catalyst morphology control is an important aspect of industrial polyolefin plant operation. Catalyst morphology characteristics influence polymer powder properties such as the bulk density, flowability, degassing and particle adhesion. Such properties greatly influence plant operation efficiency. For example, unsuitable catalyst morphology may cause failure in polymer morphology control, which can lead to serious trouble in plant operation, such as fouling or sheeting.

In addition to catalyst morphology, catalyst lifetime or the ability of a catalyst to remain active over prolonged periods of time can also be important in producing polymers with desired characteristics. Catalysts with extended lifetime, for instance, can produce polyolefin polymers and especially impact resistant polyolefin copolymers with improved and more controlled properties.

Although great advances have been made in polyolefin polymerization processes and in formulating new catalyst systems, further improvements are needed. For instance, a need exist for a polymerization process for producing polyolefin polymers with improved polymer flowability and handling. For example, polymer flowability issues are particularly prevalent when producing impact resistant polyolefin polymers that have elastomeric properties.

SUMMARY

In general, the present disclosure is directed to producing polyolefin polymers having improved flowability properties that are easier to handle and transport. Polyolefin polymers with improved flow properties, for instance, can be produced utilizing a catalyst system that not only has a prolonged and extended lifetime but can also produce polyolefin polymers having improved morphology characteristics that translate into a polymer resin that has better fluid-like properties and is easier to handle. Through the process of the present disclosure, the efficiency of the polymer production process is greatly improved.

In one embodiment, for instance, the present disclosure is directed to a polymer composition comprising a propylene-ethylene copolymer that is in the form of particles. The propylene-ethylene copolymer includes propylene as a primary monomer and contains ethylene in an amount greater than about 5% by weight, such as in an amount greater than about 8% by weight, such as in an amount greater than about 10% by weight, and generally in an amount less than about 45% by weight. The propylene-ethylene copolymer, for instance, can be a heterophasic polymer and/or can have elastomeric properties. In accordance with the present disclosure, the propylene-ethylene copolymer particles can be formulated so as to have improved flow properties such that the copolymer displays a Cup Test result of less than about 10 seconds. For example, the copolymer can display a Cup Test Index of 2 or less.

The propylene-ethylene copolymer can generally have a melt flow index of greater than about 10 g/10 min, such as greater than about 20 g/10 min, such as greater than about 30 g/10 min, such as greater than about 40 g/10 min, such as greater than about 50 g/10 min and generally less than about 500 g/10 min.

In an alternative embodiment, the present disclosure is directed to a polymer composition containing a polyolefin polymer, such as a polypropylene polymer. The polypropylene polymer is in the form of particles. The particles can have a D50 particle size of from about 150 microns to about 3000 microns, such as from about 450 microns to about 1000 microns. In accordance with the present disclosure, the particles have a particle morphology such that the particles have a B/L3 of greater than about 0.6, such as greater than about 0.68, such as greater than about 0.7, such as greater than about 0.8 and generally less than about 1. In addition, the polymer composition can have a relatively high bulk density. The bulk density, for instance, can be greater than about 0.415 g/cm$^3$, such as from about 0.42 g/cm$^3$ to about 0.6 g/cm$^3$.

The polymer particles can have a rounded shape and can be devoid of agglomerates. In one embodiment, for instance, the polymer particles may comprise microspheres.

Polyolefin polymers as described above, such as propylene-ethylene copolymers and other polypropylene polymers, can be formed using various processes. In one embodiment, for instance, the polyolefin polymer is produced in the presence of a catalyst system that includes a solid catalyst component combined with an aluminum compound, at least one selectivity control agent, and optionally an activity limiting agent. In one embodiment, the solid catalyst component comprises a reaction product of a magnesium compound with an epoxy compound. The solid catalyst component can further include an organic phosphorous compound, a titanium compound, an organosilicon compound, and an internal electron donor. The solid catalyst component can further include a supportive donor. In one embodiment, the supportive donor comprises ethyl benzoate, while the internal electron donor comprises an aryl diester.

The present disclosure is also directed to a solid catalyst component. The solid catalyst component, in one embodiment, comprises:

a magnesium compound including a halide-containing magnesium compound and a reaction product of a magnesium compound with an epoxy compound;

an organic phosphorus compound;

a titanium compound;

an organosilicon compound containing: Si—O, or O—Si—O groups;

an internal electron donor, the internal electron donor comprising an aryl diester, a 1,2-phenylene dibenzoate, a diether, a succinate, an organic acid ester, a polycarboxylic acid ester, a polyhydroxy ester, a heterocyclic polycarboxylic acid ester, an inorganic acid ester, an alicyclic polycarboxylic acid ester, a hydroxy-substituted carboxylic acid ester compound having 2 to 30 carbon atoms, or a compound having at least one ether group and at least one ketone group, or mixtures thereof;

wherein the solid catalyst component is free of side reaction products between a carboxylic acid or an anhydride thereof and a magnesium compound or a titanium compound, and wherein the solid catalyst component has a particle size from about 5 microns to about 70 microns (on a 50% by volume basis).

In another aspect, a catalyst system for use in olefinic polymerization is provided, the catalyst system comprising the solid catalyst component produced by the process of any of the above processes, an organoaluminum compound, and optionally, an organosilicon compound.

In any of the above catalyst system embodiments the organoaluminum compound may be an alkyl-aluminum compound. For example, the alkyl-aluminum compound may be a trialkyl aluminum compound such as triethylaluminum, triisobutylaluminum, or tri-n-octylaluminum.

In another aspect, a process is provided for polymerizing or copolymerizing a polypropylene monomer, the process may include contacting an olefinic monomer, or a mixture of olefinic monomers with the above catalyst system for forming a homopolymer of the olefinic monomer or a co-polymer of a mixture of olefinic monomers.

Other features and aspects of the present disclosure are discussed in greater detail below.

DETAILED DESCRIPTION

Figure 1:
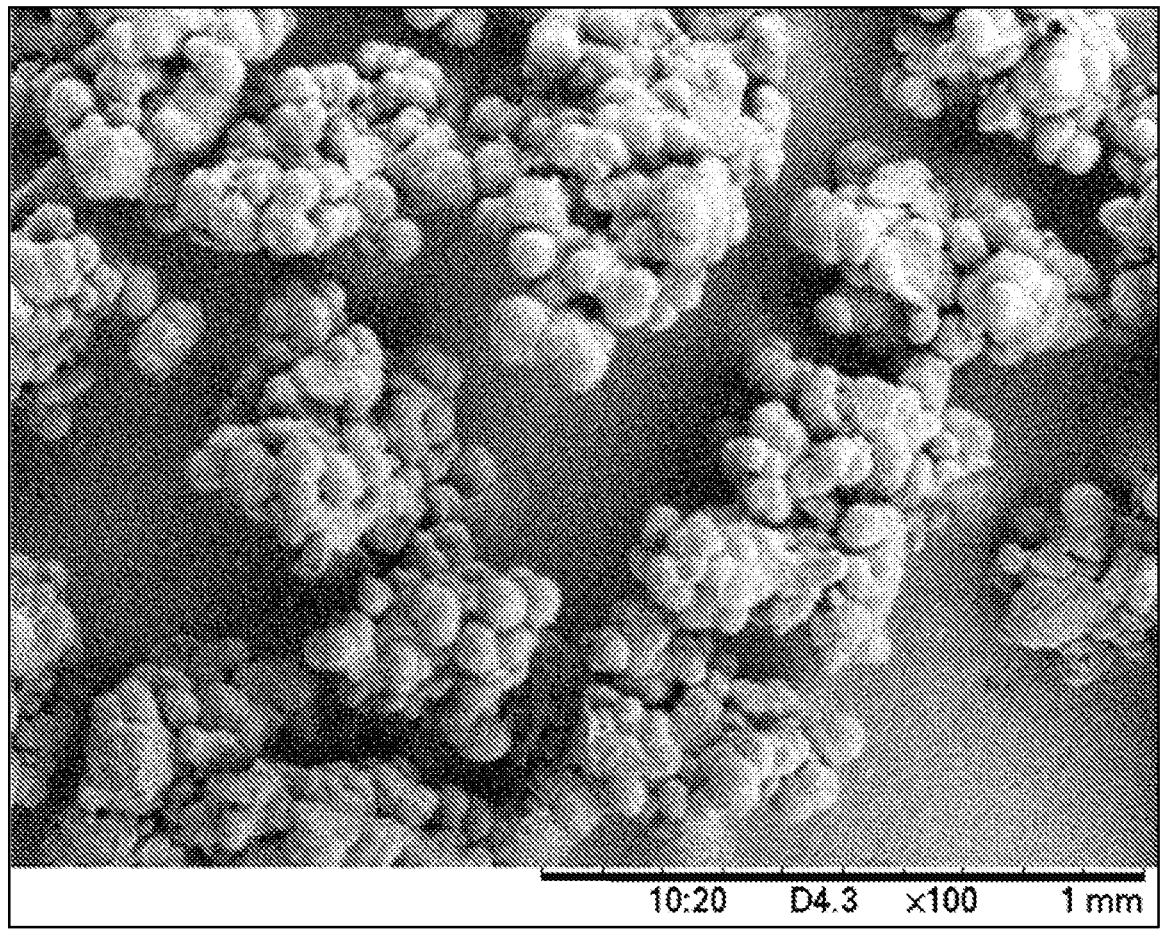
FIG. 1 shows a microscopic view of the polymer produced with the catalyst component of Example 5 (Comparative).

Before describing several exemplary embodiments, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment. Thus, the appearances of the phrases such as "in one or more embodiments," "in certain embodiments," "in one embodiment" or "in an embodiment" in various places throughout this specification are not necessarily referring to the same embodiment. Furthermore, the particular features, structures, materials, or characteristics may be combined in any suitable manner in one or more embodiments.

Although reference herein is to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

In general, the present disclosure is directed to polyolefin polymers having improved flow properties. For example, the polyolefin polymers can be produced in the form of particles that have fluid-like properties that provide various advantages and benefits. The polymer particles, for instance, improve process efficiency, reduce waste, and allow for the polyolefin polymers to be easily handled and transported.

In accordance with the present disclosure, polyolefin polymer resins are produced having improved flow properties by, in one embodiment, carefully controlling the particle morphology during polymerization. In an alternative embodiment, the flow properties of the polyolefin polymer can be improved by utilizing a catalyst with an extended catalytic lifetime. Utilizing a catalyst with extended and robust activity has been found to produce polyolefin polymers, particularly polypropylene random copolymers, that have a particle construction that prevents the particles from agglomerating or otherwise sticking together for providing the polymer resin with dramatically improved flow properties. As will be described in greater detail below, in one embodiment, the polyolefin particles of the present disclosure are formed in the presence of a Ziegler-Natta catalyst formed from a magnesium compound, a titanium compound, epoxy, and one or more internal electron donors and/or supportive donors.

In one embodiment, a polypropylene polymer is formed in accordance with the present disclosure having a controlled particle morphology. In particular, the polypropylene particles can be formed having a more rounded or spherical shape in conjunction with a relatively high bulk density that improves the polymer production process and dramatically improves polymer flowability.

For example, in one embodiment, the polypropylene polymer particles have a D50 particle size of greater than about 400 microns, such as greater than about 500 microns, such as greater than about 600 microns, such as greater than about 700 microns, and generally less than about 1500 microns, such as less than about 1200 microns, such as less than about 1000 microns. The polymer particles can have a rounded shape. The particle morphology, for instance, is such that the particles have an aspect ratio, such as a B/L3 value of greater than about 0.6, such as greater than about 0.68, such as greater than about 0.7, such as greater than about 0.75, such as greater than about 0.8, and generally less than about 1. For instance, the polymer particles can be devoid of agglomerations and can have a substantially spherical shape. In one embodiment, for instance, the polymer particles form microspheres.

In addition to having a rounded shape, the polymer particles can also have a relatively high bulk density. The bulk density of the particles, for instance, can be greater than about 0.415 g/cm$^3$. For instance, the bulk density of the polymer particles can be greater than about 0.42 g/cm$^3$, such as greater than about 0.44 g/cm$^3$, such as greater than about 0.46 g/cm$^3$, such as greater than about 0.48 g/cm$^3$. The bulk density is generally less than about 0.6 g/cm$^3$.

The above particle shape and morphology has been found to improve flowability and handling of the polymer. In various embodiments, the polymer can comprise a homopolymer or copolymer. The copolymer, for instance, may comprise a propylene-ethylene random copolymer. In one embodiment, the polymer particles are formed in a polymerization process using a catalyst that has a rounded shape and improved morphology.

In addition to forming polymer particles having a desired size and shape as described above, in an alternative embodiment, the flowability of elastomeric polypropylene copolymers can be improved using the same or similar catalyst. Although unknown, it is believed that using a catalyst having an extended lifetime or activity can facilitate the production of a propylene random copolymer having rubber-like characteristics with excellent flow properties. The propylene random copolymer, for instance, can be formed using multiple reactors, such as at least two different reactors in order to produce a copolymer having elastomeric properties. Through the process of the present disclosure, the polypropylene random copolymer can be produced that not only easily transfers from a first reactor to a second reactor, but can also be easily handled and removed from the final reactor due to the improvement in flowability.

For example, in one embodiment, the polypropylene random copolymer may comprise a propylene-ethylene copolymer containing ethylene in an amount greater than about 3% by weight, such as greater than about 5% by weight, such as in an amount greater than about 8% by weight, such as in an amount greater than about 10% by weight, and generally in an amount less than about 45% by weight. The propylene-ethylene random copolymer can be a heterophasic polymer that has elastomeric properties. Such polymers have excellent impact strength resistance but tend to have rather adverse flowability characteristics. Propylene-ethylene copolymers made in accordance with the present disclosure, however, can have flow properties such that the copolymer exhibits a Cup Test result of less than about 10 seconds, such as less than about 9 seconds, such as less than about 8 seconds. For example, the propylene-ethylene copolymer can display a Cup Test Index of 2 or less. The Cup Test is a method that measures powder flowability, especially of high rubber content polypropylene copolymer powders.

The propylene-ethylene copolymer can have a melt flow rate of from about 1 g/10 min to about 1000 g/10 min. For instance, the copolymer can have a melt flow rate of greater than about 10 g/10 min, such as greater than about 20 g/10 min, such as greater than about 30 g/10 min, such as greater than about 40 g/10 min, such as greater than about 50 g/10 min. The melt flow rate is generally less than about 500 g/10 min, such as less than about 400 g/10 min, such as less than about 300 g/10 min, such as less than about 200 g/10 min. In one embodiment, the melt flow rate can be from about 50 g/10 min to about 150 g/10 min.

Embodiments of Catalyst Systems Used to Produce Polyolefin Polymers

Described herein are Ziegler-Natta catalyst systems and supports for Ziegler-Natta catalysts and methods of making the same. One aspect of the catalyst systems is a solid catalyst component containing a halide-containing magnesium compound and titanium compound for polymerizing an olefin, where the solid catalyst component has substantially spherical or spheroidal shape. The solid catalyst component can be used to form a competent Ziegler-Natta catalyst in combination with one or more external and/or internal electron donors and an organoaluminum compound.

As used throughout this disclosure, the term "solid catalyst component" refers to a pre-catalyst containing a halide-containing magnesium compound and titanium compound, and optionally one or more internal electron donors that are useful for forming a competent Ziegler-Natta catalyst system upon combination with a main group metal alkyl.

In a typical manner of employing the Ziegler-Natta catalyst system, a solid catalyst component, an electron donor, and an organoaluminum compound (a main group metal alkyl) form a slurry catalyst system, which can contain any suitable liquid such as an inert hydrocarbon medium. Examples of inert hydrocarbon media include aliphatic hydrocarbons such as propane, butane, pentane, hexane, heptane, octane, decane, dodecane and kerosene; alicyclic hydrocarbons such as cyclopentane, cyclohexane and methylcyclopentane; aromatic hydrocarbons such as benzene, toluene and xylene; halogenated hydrocarbons such as ethylene chloride and chlorobenzene; and mixtures thereof. The slurry medium can be hexane, heptane or mineral oil. The slurry medium can be different from the diluent used in forming the mixture from which the solid catalyst component is precipitated.

The herein described solid catalyst supports can be utilized in any suitable Ziegler-Natta polymerization catalyst system. Ziegler-Natta catalyst systems include a reagent or combination of reagents that are functional to catalyze the polymerization of 1-alkenes (α-olefins) to form polymers, typically with high isotacticity, when pro-chiral 1-alkenes are polymerized. The term "Ziegler-Natta catalyst" refers to any composition having a transition metal and a main group metal alkyl component capable of supporting catalysis of 1-alkene polymerization. The transition metal component is typically a Group IV metal such as titanium, or vanadium, the main group metal alkyl is typically an organoaluminum compound having a carbon-Al bond, and the electron donor can be any of numerous compounds including aromatic esters, alkoxysilanes, amines and ketones can be used as external donors added to the transition metal component and the main group metal alkyl component or an appropriate internal donor added to the transition metal component and the main group metal alkyl component during synthesis of those components.

Described herein are methods of making a solid catalyst component for use in a Ziegler-Natta catalyst, and the methods and catalysts are free of carboxylic acid or anhydrides. By being free of the carboxylic acids and/or anhydrides, the catalysts provide high activity due to absence of side products of the reaction between the carboxylic acid and/or anhydride with the magnesium compounds and $TiCl_4$, that may otherwise result in the deactivation of active centers in polymerization process.

The catalyst/support morphology is a key factor to consider in any commercial polymer production process. To control the catalyst/support morphology variable techniques and processes are used. One such technique is to use a surfactant during the support formation. Surfactants are compounds that lower the surface tension (or interfacial tension) between two liquids or between a liquid and a solid. Surfactants are usually polar organic compounds, and they can be removed from the solid catalyst or can partly stay on the catalyst surface. Surfactants may also act as a supportive internal donor interacting with the main internal donor or act as a negative component deactivating catalytic active center during the polymerization process.

In a first aspect, a process is provided for preparing a solid catalyst component for the production of a polyolefin, such as a polypropylene. The processes include dissolving a halide-containing magnesium compound in a mixture, where the mixture includes epoxy compound, an organic phosphorus compound, and a first hydrocarbon solvent to form a homogenous solution. The homogenous solution is then treated with a first titanium compound in the presence of an organosilicon compound and optionally with a non-phthalate electron donor and/or supportive donor, and, to form a solid precipitate. The solid precipitate is then treated with a second titanium compound in the presence of a non-phthalate electron donor to form the solid catalyst component. The process is to be conducted free of carboxylic acids and anhydrides. Additionally, the dissolving and treating of the homogeneous solution may be performed sequentially or simultaneously. Finally, the first and second titanium compounds are, independently, represented as:

$$Ti(OR)_g X_{4-g}$$

where each R is independently a $C_1$-$C_4$ alkyl; X is Br, Cl, or I; and g is 0, 1, 2, 3, or 4.

The halide-containing magnesium compound, epoxy compound, and organic phosphorus compound are reacted in the presence of a hydrocarbon solvent. The hydrocarbon solvent can include aromatic or non-aromatic solvents or combinations thereof. In certain embodiments, the aromatic hydrocarbon solvent is selected from toluene and C2-C20 alkylbenzene. In certain embodiments, the nonaromatic hydrocarbon solvent is selected from hexane and heptane. In an embodiment, the hydrocarbon solvent is a mixture of toluene and hexane. In another embodiment, the hydrocarbon solvent is a mixture of ethylbenzene and heptane. In certain embodiments, a ratio of the non-aromatic solvent to the aromatic solvent is from 10:90 to 90:10 wt % or 30:70 to 70:30 wt % or 40:60 to 65:35 wt % or 50:50 to 45:55 wt %.

In a particular embodiment, the halide-containing magnesium compound, epoxy compound, and organic phosphorus compound are reacted in the presence of an organic solvent at a first temperature from about 25 to about 100° C. to form a homogenous solution. In another embodiment, the first temperature is from about 40 to about 90° C. or from about 50 to about 70° C. In a certain embodiment, the molar ratio of the magnesium compound to alkylepoxide is from about 0.1:2 to about 2:0.1 or about 1:0.25 to about 1:4 or about 1:0.9 to about 1:2.2. In a certain embodiment, the molar ratio of the magnesium compound to the Lewis base is from about 1:0.1 to about 1:4 or 0.5:1 to 2.0:1 or 1:0.7 to 1:1. Without wishing to be bound by any theory, it is believed that a halogen atom is transferred from the magnesium compound to the epoxy compound to open the epoxide ring and form an alkoxide magnesium species having a bond between the magnesium atom and the oxygen atom of the newly formed alkoxide group. During this process the organic phosphorus compound coordinates to Mg atom of halide-containing magnesium compound and increases the solubility of the magnesium-containing species present.

The process for preparing the solid catalyst component may also include addition of an organosilicon compound during, or after, the dissolution of the magnesium compound (Mg-compound) in the organic solvent, along with the epoxy compound. The organosilicon compound may be a silane, a siloxane, or a polysiloxane. The organosilicon compound, in some embodiments, may be represented as Formula (II):

$$R_n\text{—Si(OR')}_{4-n} \tag{II}$$

In Formula (II) each R may be H, alkyl, or aryl; each R' may be H, alkyl, aryl, or —SiR$_n$(OR')$_{3-n}$, where n is 0, 1, 2, or 3.

In some embodiments, the organosilicon is a monomeric or polymeric compound. The organosilicon compound may contain —Si—O—Si— groups inside of one molecule or between others. Other illustrative examples of an organosilicon compound include polydialkylsiloxane and/or tetraalkoxysilane. Such compounds may be used individually or as a combination thereof. The organosilicon compound may be used in combination with aluminum alkoxides and a first internal donor. In some embodiments, polydimethylsiloxane and/or tetraethoxysilane may be used.

The aluminum alkoxide referred to above may be of formula Al(OR')$_3$ where each R' is individually a hydrocarbon with up to 20 carbon atoms. This may include where each R' is individually methyl, ethyl, n-propyl, iso-propyl, n-butyl, sec-butyl, tert-butyl, n-pentyl, iso-pentyl, neo-pentyl, etc. It is believed that the organosilicon compound reacts with the aluminum oxide during the catalyst component preparation, thereby forming compounds containing Al—O—Si—O linkages. Therefore, these compounds can be prepared before the catalyst component synthesis and added directly to the process.

The organosilicon compound helps to precipitate the solid catalyst component from the solution. It is believed that the Si—O groups from the organosilicon compound coordinate to Mg atoms of the Mg-compound during the precipitation of solid catalyst component, thereby leading to a desired catalyst component morphology. This type of coordination is usually weak. Therefore, during the treatment of the solid catalyst component with the second Ti-compound and the second non-phthalate internal donor, they displace the organosilicon compound from the Mg compound, providing the high activity catalyst component.

It is known that the precipitation of the solid catalyst component using Mg compounds in an epoxy medium containing anhydrides or organic acids result in the certain side products containing derivatives formed by interaction of epoxy compounds with anhydrides or organic acids. These derivatives contain carbonyl groups coordinated strongly to Mg-atom and can be present on the final catalyst component, and lead to deactivation the catalyst active centers. The above catalyst systems, which are free of organic acids and/or anhydrides, address these deficiencies of the earlier systems.

The halide-containing magnesium compound in the homogenous solution is treated with a titanium halide compound to form a solid precipitate. The solution can be heated and a surface modifier can be added to control phase morphology. Also, when treating with a titanium halide compound, a non-phthalate electron donor is added. The electron donor changes the viscosity and polarity of the solution that effects on the morphology precipitated particles, in particular, particle size, particle shape and particle density.

As noted above, the process is carried out in the presence of non-phthalate donors. In one embodiment, a supportive donor is used that may also be referred to as the first non-phthalate donor. The supportive donor or first non-phthalate donor may be a diether, succinate, diester, oxygen-containing electron donor such as an organic ester, polyester, polyhydroxy ester, heterocyclic polyester, inorganic esters, alicyclic polyester, and hydroxy-substituted esters having 2 to about 30 carbon atoms.

Illustrative first non-phthalate donors or supportive donors include methyl formate; ethyl acetate; vinyl acetate; propyl acetate; octyl acetate; cyclohexyl acetate; ethyl propionate; methyl butyrate; ethyl valerate; ethyl stearate; methyl chloroacetate; ethyl dichloroacetate; methyl methacrylate; ethyl crotonate; dibutyl maleate; diethyl butylmalonate; diethyl dibutylmalonate; ethyl cyclohexanecarboxylate; diethyl 1,2-cyclohexanedicarboxylate; di-2-ethylhexyl 1,2-cyclohexanedicarboxylate; methyl benzoate; ethyl benzoate; propyl benzoate; butyl benzoate; octyl benzoate; cyclohexyl benzoate; phenyl benzoate; benzyl benzoate; methyl toluate; ethyl toluate; amyl toluate; ethyl ethylbenzoate; methyl anisate; ethyl anisate; ethyl ethoxybenzoate, γ-butyrolactone; δ-valerolactone; coumarine; phthalide; ethylene carbonate; ethyl silicate; butyl silicate; vinyltriethoxysilane; phenyltriethoxysilane; diphenyldiethoxysilane; diethyl 1,2-cyclohexanecarboxylate; diisobutyl 1,2-cyclohexanecarboxylate; diethyl tetrahydrophthalate and nadic acid; diethyl ester; diethyl naphthalenedicarboxylate; dibutyl naphthlenedicarboxylate; triethyl trimellitate and dibutyl trimellitate; 3,4-furanedicarboxylic acid esters; 1,2-diacetoxybenzene; 1-methyl-2,3-diacetoxybenzene; 2-methyl-2,3-diacetoxybenzene; 2,8-diacetoxynaphthalene; ethylene glycol dipivalate; butanediol pivalate; benzoylethyl salicylate; acetylisobutyl salicylate; acetylmethyl salicylate; diethyl adipate; diisobutyl adipate; diisopropyl sebacate; di-n-butyl sebacate; di-n-octyl sebacate; or di-2-ethylhexyl sebacate. In some embodiments, the first non-phthalate donor is methyl formate, butyl formate, ethyl acetate, vinyl acetate, propyl acetate, octyl acetate, cyclohexyl acetate, ethyl propionate, methyl butyrate, ethyl butyrate, isobutyl butyrate, ethyl valerate, ethyl stearate, methyl chloroacetate, ethyl dichloroacetate, ethyl acrylate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, ethyl p-methoxybenzoate, methyl p-methyl benzoate, ethyl p-t-butyl benzoate, ethyl naphthoate, methyl toluate, ethyl toluate, amyl toluate, ethyl ethyl benzoate, methyl anisate, ethyl anisate, or ethyl ethoxybenzoate.

The combination of different supportive donors or first internal donors and solvents can be used to produce a catalyst component with different morphology: i.e. granular and/or spherical. In particular, a catalyst component with granular support may be produced using mono-ester as a first internal donor with an aromatic or hydrocarbon solvent, while spherical type catalyst components may be produced using two or three different internal donors (e.g. mono-ester, dialkyl ether and acrylates) in a mixture of two solvents (aromatic and hydrocarbons).

In one embodiment, a supportive donor or first internal electron donor is used in conjunction with a second non-phthalate electron donor. Second non-phthalate electron donors may include compounds that are different from the first non-phthalate electron donor and is a compound that is a diether, succinate, oxygen-containing electron donors such as organic ester, polyester, polyhydroxy ester, heterocyclic polyester, inorganic esters, alicyclic polyester, and hydroxy-substituted esters having 2 to about 30 carbon atoms, or a compounding having at least one ether group and at least one ketone group. In some embodiments, the second non-phthalate donor is selected from the group consisting of linear of cyclic diethers, and non-phthalate aromatic diesters. In another embodiment, the second internal electron donor may be a dibenzoate, a dialkylate, and/or diarylate.

Additional illustrative second non-phthalate electron donors may include, alone or in combination with any of the above, compounds represented by the following formulas:

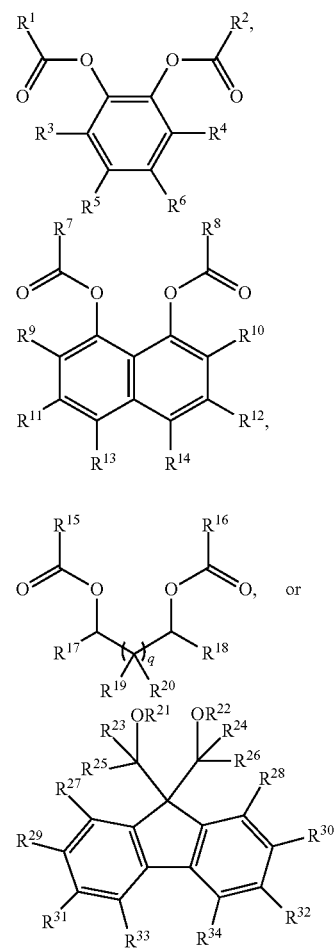

where each of $R^1$ through $R^{34}$ is independently H, F, Cl, Br, I, $OR^{33}$, alkyl, cycloalkyl, cycloalkylalkyl, aryl, aralkyl, heterocyclyl, heterocyclylalkyl, heteroaryl, or heteroarylalkyl; q is an integer from 0 to 12, wherein $R^{33}$ is a alkyl or heteroalkyl. Other non-phthalate donors may also include those as listed as internal electron donors in U.S. Pat. No. 9,045,570, incorporated by reference herein.

Examples of the halide-containing magnesium compounds include magnesium chloride, magnesium bromide, magnesium iodide, and magnesium fluoride. In one embodiment, the halide-containing magnesium compound is magnesium chloride.

Illustrative of the epoxy compounds include, but are not limited to, glycidyl-containing compounds of the Formula:

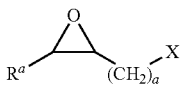

wherein "a" is from 1, 2, 3, 4, or 5, X is F, Cl, Br, I, or methyl, and $R^a$ is H, alkyl, aryl, or cyclyl. In one embodiment, the alkylepoxide is epichlorohydrin. In some embodiments, the epoxy compound is a haloalkylepoxide or a nonhaloalkylepoxide.

According to some embodiments, the epoxy compound is selected from the group consisting of ethylene oxide; propylene oxide; 1,2-epoxybutane; 2,3-epoxybutane; 1,2-epoxyhexane; 1,2-epoxyoctane; 1,2-epoxydecane; 1,2-epoxydodecane; 1,2-epoxytetradecane; 1,2-epoxyhexadecane; 1,2-epoxyoctadecane; 7,8-epoxy-2-methyloctadecane; 2-vinyl oxirane; 2-methyl-2-vinyl oxirane; 1,2-epoxy-5-hexene; 1,2-epoxy-7-octene; 1-phenyl-2,3-epoxypropane; 1-(1-naphthyl)-2,3-epoxypropane; 1-cyclohexyl-3,4-epoxybutane; 1,3-butadiene dioxide; 1,2,7,8-diepoxyoctane; cyclopentene oxide; cyclooctene oxide; α-pinene oxide; 2,3-epoxynorbornane; limonene oxide; cyclodecane epoxide; 2,3,5,6-diepoxynorbornane; styrene oxide; 3-methyl styrene oxide; 1,2-epoxybutylbenzene; 1,2-epoxyoctylbenzene; stilbene oxide; 3-vinyl styrene oxide; 1-(1-methyl-1,2-epoxyethyl)-3-(1-methylvinyl benzene); 1,4-bis(1,2-epoxypropyl) benzene; 1,3-bis(1,2-epoxy-1-methylethyl)benzene; 1,4-bis(1,2-epoxy-1-methylethyl)benzene; epifluorohydrin; epichlorohydrin; epibromohydrin; hexafluoropropylene oxide; 1,2-epoxy-4-fluorobutane; 1-(2,3-epoxypropyl)-4-fluorobenzene; 1-(3,4-epoxybutyl)-2-fluorobenzene; 1-(2,3-epoxypropyl)-4-chlorobenzene; 1-(3,4-epoxybutyl)-3-chlorobenzene; 4-fluoro-1,2-cyclohexene oxide; 6-chloro-2,3-epoxybicyclo[2.2.1]heptane; 4-fluorostyrene oxide; 1-(1,2-epoxypropyl)-3-trifluorobenzene; 3-acetyl-1,2-epoxypropane; 4-benzoyl-1,2-epoxybutane; 4-(4-benzoyl)phenyl-1,2-epoxybutane; 4,4'-bis(3,4-epoxybutyl)benzophenone; 3,4-epoxy-1-cyclohexanone; 2,3-epoxy-5-oxobicyclo[2.2.1]heptane; 3-acetylstyrene oxide; 4-(1,2-epoxypropyl) benzophenone; glycidyl methyl ether; butyl glycidyl ether; 2-ethylhexyl glycidyl ether; allyl glycidyl ether; ethyl 3,4-epoxybutyl ether; glycidyl phenyl ether; glycidyl 4-tert-butylphenyl ether; glycidyl 4-chlorophenyl ether; glycidyl 4-methoxyphenyl ether; glycidyl 2-phenylphenyl ether; glycidyl 1-naphthyl ether; glycidyl 2-phenylphenyl ether; glycidyl 1-naphthyl ether; glycidyl 4-indolyl ether; glycidyl N-methyl-α-quinolon-4-yl ether; ethyleneglycol diglycidyl ether; 1,4-butanediol diglycidyl ether; 1,2-diglycidyloxybenzene; 2,2-bis(4-glycidyloxyphenyl)propane; tris(4-glycidyloxyphenyl)methane; poly(oxypropylene)triol triglycidyl ether; a glycidic ether of phenol novolac; 1,2-epoxy-4-methoxycyclohexane; 2,3-epoxy-5,6-dimethoxybicyclo[2.2.1]heptane; 4-methoxystyrene oxide; 1-(1,2-epoxybutyl)-2-phenoxybenzene; glycidyl formate; glycidyl acetate; 2,3-epoxybutyl acetate; glycidyl butyrate; glycidyl benzoate; diglycidyl terephthalate; poly(glycidyl acrylate); poly(glycidyl methacrylate); a copolymer of glycidyl acrylate with another monomer; a copolymer of glycidyl methacrylate with another monomer; 1,2-epoxy-4-methoxycarbonylcyclohexane; 2,3-epoxy-5-butoxycarbonylbicyclo[2.2.1]heptane; ethyl 4-(1,2-epoxyethyl)benzoate; methyl 3-(1,2-epoxybutyl)benzoate; methyl 3-(1,2-epoxybutyl)-5-pheylbenzoate; N,N-glycidyl-methylacetamide; N,N-ethylglycidylpropionamide; N,N-glycidylmethylbenzamide; N-(4,5-epoxypentyl)-N-methyl-benzamide; N,N-diglycylaniline; bis(4-diglycidylaminophenyl)methane; poly(N,N-glycidylmethylacrylamide); 1,2-epoxy-3-(diphenylcarbamoyl)cyclohexane; 2,3-epoxy-6-(dimethylcarbamoyl)bicycle[2.2.1]heptane; 2-(dimethylcarbamoyl)styrene oxide; 4-(1,2-epoxybutyl)-4'-(dimethylcarbamoyl)biphenyl; 4-cyano-1,2-epoxybutane; 1-(3-cyanophenyl)-2,3-epoxybutane; 2-cyanostyrene oxide; and 6-cyano-1-(1,2-epoxy-2-phenylethyl)naphthalene.

As an example of the organic phosphorus compound, phosphate acid esters such as trialkyl phosphate acid ester may be used. Such compounds may be represented by Formula:

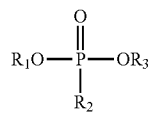

wherein $R_1$, $R_2$, and $R_3$ are each independently selected from the group consisting of methyl, ethyl, and linear or branched ($C_3$-$C_{10}$) alkyl groups. In one embodiment, the trialkyl phosphate acid ester is tributyl phosphate acid ester.

The halide-containing magnesium compound, epoxy compound, and organic phosphorus compound are contacted in the presence of a hydrocarbon solvent. The hydrocarbon solvent can include aromatic or non-aromatic solvents or combinations thereof. In certain embodiments, the aromatic hydrocarbon solvent is selected from toluene and $C_2$-$C_{20}$ alkylbenzene. In certain embodiments, the nonaromatic hydrocarbon solvent is selected from hexane and heptane. In an embodiment, the hydrocarbon solvent is a mixture of toluene and hexane. In another embodiment, the hydrocarbon solvent is a mixture of ethylbenzene and heptane. In certain embodiments, a ratio of the non-aromatic solvent to the aromatic solvent is from 10:90 to 90:10 wt % or 30:70 to 70:30 wt % or 40:60 to 65:35 wt % or 50:50 to 45:55 wt %.

In a particular embodiment, the halide-containing magnesium compound, epoxy compound, and organic phosphorus compound are contacted in the presence of an organic solvent at a first temperature from about 25 to about 100° C. to form a homogenous solution. In another embodiment, the first temperature is from about 40 to about 90° C. or from about 50 to about 70° C. In a certain embodiment, the molar ratio of the magnesium compound to alkylepoxide is from about 0.1:2 to about 2:0.1 or about 1:0.25 to about 1:4 or about 1:0.9 to about 1:2.2. In a certain embodiment, the molar ratio of the magnesium compound to the Lewis base is from about 1:0.1 to about 1:4 or 0.5:1 to 2.0:1 or 1:0.7 to 1:1. Without wishing to be bound by any theory, it is believed that a halogen atom is transferred from the magnesium compound to the epoxy compound to open the epoxide ring and form an alkoxide magnesium species having a bond between the magnesium atom and the oxygen atom of the newly formed alkoxide group. The organic phosphorus compound functions to increase the solubility of the magnesium-containing species present.

After formation, the homogenous solution can be optionally treated with a halogenating agent. The halogenating agent can be an organic or inorganic compound containing at least one halogen atom that can be transferrable to a magnesium atom. In particular embodiments, the halogenating agent contains chlorine. In particular embodiments, the halogenating agent is selected from arynoyl chlorides, alkanoyl chlorides, and alkyl chlorides. In certain embodiments, the halogenating agent is selected from benzoyl chloride, furoyl chloride, acetyl chloride, linear or branched ($C_1$-$C_6$) alkyl chloride, and ($C_1$-$C_6$) alkanoyl chloride. In one embodiment, the halogenating agent may be phthaloyl chloride. In other embodiments, however, the catalyst composition can be completely phthalate-free. In other embodiments, the halogenating agent is selected from HCl, $TiCl_4$, $R_nTiCl_{4-n}$, $SiCl_4$, $R_nSiCl_{4-n}$, and $R—AlCl_{4-n}$, wherein R represents an alkyl, cycloalkyl, aromatic or alkoxy, and n is a whole number satisfying the formula 0<n<4. In certain embodiments the ratio of halogenating agent to magnesium compound is at least 1:1 mol ratio.

The molar ratio of the first titanium compound added to the halide-containing magnesium compound may be from about 3:1 to about 15:1, or from about 5:1 to about 10:1.

The magnesium-containing solution formed during the reaction of the halide-containing magnesium compound, epoxy compound, organic phosphorus compound and organosilicon compound can be in the form of dispersions, colloids, emulsions, and other two-phase systems. The homogenous solution can be emulsified using conventional emulsion techniques including one or more of agitation, stirring, mixing, high and/or low shear mixing, mixing nozzles, atomizers, membrane emulsification techniques, milling sonication, vibration, microfluidization, and the like.

The magnesium-containing species phase is dispersed within the solvent phase. The size and shape of droplets forming the magnesium phase can be controlled through a combination of adjusting the temperature, adjusting the amount of solvent, adjusting the agitation energy, and including/excluding various additives, including the surface modifier. The temperature during the titanium compounds addition is from about −35° C. to about 15° C. After phase separation and/or titanium compound addition, the mixture is raised to a higher temperature. In one embodiment, the higher temperature is from about 15° C. to about 100° C. In another embodiment, the temperature is from about 20° C. to about 90° C. or from about 50° C. to about 85° C. or from about 60° C. to 85° C. In an embodiment, while the mixture is between the lower and higher temperatures, a surface modifier is added to facilitate formation of spherical droplets of the magnesium phase surrounded by the solvent phase. That is, the addition of a surface modifier can assist in controlling the morphology of the droplets of the magnesium phase.

During addition of the titanium halide compound to the magnesium solution which contains associated molecules or groups of molecules of the magnesium alkoxide with coordinated organic phosphorus compound, organosilicon compound and molecules of solvent, the reaction occurs between the magnesium alkoxide and the titanium halide compound forming the magnesium halide and complexes of the magnesium halide with titanium halide compound and the titanium alkoxide.

At the beginning of the reaction (usually at low temperature: (−35 to −20° C.)) the newly formed associated groups of the magnesium halide molecules and complexes of the magnesium halide with titanium halide compound and the titanium alkoxide are present in "oil phase-droplets" (higher viscosity liquid than other media (solvent) around). During the continuation of the reaction (the reaction temperature is raised to 0-40° C.) the magnesium halide molecules and complexes of the magnesium halide with titanium halide compound and the titanium alkoxide in the oil phase are crystallized. The crystallization process is usually completed at temperatures of 50-100° C. forming the solid intermediate catalyst component.

The morphology of the solid intermediate catalyst component (and the catalyst component) (particle size and shape) depends on many factors including the polarity of solvent, presence of reagents to control precipitation, surfactants, additives and others.

In particular, the size and shape of droplets forming the magnesium phase can be controlled through a combination of adjusting the temperature, amount of solvent, adjusting the agitation energy, and including/excluding various additives, including the surface modifier and temperature of the precipitation.

The catalyst component morphology and catalyst performances are sufficiently controlled by addition of the supportive electron donor (or donors). The supportive electron donor is an organic compound containing an oxygen atom and has the ability to coordinate to magnesium atoms of magnesium in "oil phase-droplets" and allows control of the precipitation process of the solid catalyst component with desired morphology.

In one embodiment, the supportive electron donor only controls the precipitation process and the catalyst component morphology and is not incorporated into the catalyst component.

In other embodiments, the supportive electron donor controls the precipitation process and catalyst component morphology and is incorporated in the catalyst component. Therefore, the supportive electron donor and the electron donor can both define the catalyst performance in polymerization process. The supportive electron donors are usually weaker than the electron donors.

The combination of the organosilicon compound and the supportive electron donor during the precipitation of the solid catalyst intermediate allow to make the catalyst component with desired granular or spherical shape morphology.

The granular catalyst component morphology can be prepared with a raspberry shape, rounded raspberry shape, rounded shape and substantially spherical shape (microspheres) by variation of the organosilicon compounds, supportive electron donors and the conditions of the precipitation of the solid catalyst intermediate. The particle sizes of the catalyst component are from about 5 microns to about 70 microns (on a 50% by volume basis) and depend on the conditions of the precipitation (temperature, agitation speed, solvent and others) and type and amount of the supportive donor.

The supportive electron donor is selected from carboxylic monoesters methyl formate, butyl formate, ethyl acetate, vinyl acetate, propyl acetate, octyl acetate, cyclohexy acetate, ethyl propionate, methyl butyrate, ethyl butyrate, isobutyl butyrate, ethyl valerate, ethyl stearate, methyl chloroacetate, ethyl dichloroacetate, ethyl acrylate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, ethyl p-methoxybenzoate, methyl p-methylbenzoate, ethyl p-t-butylbenzoate, ethyl naphthoate, methyl toluate, ethyl toluate, amyl toluate, ethyl ethylbezoate, methyl anisate, ethyl anisate, or ethyl ethoxybenzoate.

Combining the halide-containing magnesium compound, epoxy compound, organic phosphorus compound, titanium halide and hydrocarbon solvent might create an emulsion with two phases: the solvent phase and the magnesium-titanium oil phase and with proper selection of the solvent and reagents. This process can be used to prepare a spherical morphology. Phase separation is accomplished by proper solvent selection. Solvent selection involves considering one or more of physical properties differences in polarity, density, and surface tension among others causing the separation between the solvent and the magnesium phase. Toluene is an organic solvent diluent that has been used for the formation of solid titanium catalyst components; however, use of toluene does not always promote the formation of two phases. Also, it has been discovered that the use of other alkylbenzene compounds, hexane, and heptane as a solvent or mixture of aromatic and hydrocarbons can be used and result in the formation of a solvent phase and a magnesium phase. The two phases are maintained upon subsequent addition of the titanium compound. The combination of two or more different supportive donors allow producing the solid catalyst component with spherical types.

Di-($C_1$-$C_{12}$)-alkylether in combination with acrylates (surface modifier) are used as the supportive electron donors to prepare the spherical type catalyst component.

General examples of the surface modifier include polymer surfactants, such as polyacrylates, polymethacrylates, polyalkyl methacrylates, or any other surfactant that can stabilize and emulsify. Surfactants are known in the art, and many surfactants are described in McCutcheon's "Volume I: Emulsifiers and Detergents", 2001, North American Edition, published by Manufacturing Confectioner Publishing Co., Glen Rock, N.J., and in particular, pp. 1-233 which describes a number of surfactants and is hereby incorporated by reference for the disclosure in this regard. A polyalkyl methacrylate is a polymer that may contain one or more methacrylate monomers, such as at least two different methacrylate monomers, at least three different methacrylate monomers, etc. Moreover, the acrylate and methacrylate polymers may contain monomers other than acrylate and methacrylate monomers, so long as the polymer surfactant contains at least about 40% by weight acrylate and methacrylate monomers.

Examples of monomers that can be polymerized using known polymerization techniques into polymer surfactants include one or more of an acrylate; tert-butyl acrylate; n-hexyl acrylate; methacrylate; methyl methacrylate; ethyl methacrylate; propyl methacrylate; isopropyl methacrylate; n-butyl methacrylate; t-butyl methacrylate; isobutyl methacrylate; pentyl methacrylate; isoamyl methacrylate; n-hexyl methacrylate; isodecyl methacrylate; lauryl methacrylate; stearyl methacrylate; isooctyl acrylate; lauryl acrylate; stearyl acrylate; cyclohexyl acrylate; cyclohexyl methacrylate; methoxyethyl acrylate; isobenzyl acrylate; isodecyl acrylate; n-dodecyl acrylate; benzyl acrylate; isobornyl acrylate; isobornyl acrylate; isobornyl methacrylate; 2-hydroxyethyl acrylate; 2-hydroxypropyl acrylate; 2-methoxyethyl acrylate; 2-methoxybutyl acrylate; 2-(2-ethoxyethoxy) ethyl acrylate; 2-phenoxyethyl acrylate; tetrahydrofurfuryl acrylate; 2-(2-phenoxyethoxy)ethyl acrylate; methoxylated tripropylene glycol monacrylate; 1,6-hexanediol diacrylate; ethylene glycol dimethacrylate; diethylene glycol dimethacrylate; triethylene glycol dimethacrylate; polyethylene glycol dimethacrylate; butylene glycol dimethacrylate; trimethylolpropane-3-ethoxylate triacrylate; 1,4-butanediol diacrylate; 1,9-nonanediol diacrylate; neopentyl glycol diacrylate; tripropylene glycol diacrylate; tetraethylene glycol diacrylate; heptapropylene glycol diacrylate; trimethylol propane triacrylate; ethoxylated trimethylol propane triacrylate; pentaerythritol triacrylate; trimethylolpropane trimethacrylate; tripropylene glycol diacrylate; pentaerythritol tetraacrylate; glyceryl propoxy triacrylate; tris(acryloyloxyethyl)phosphate; 1-acryloxy-3-methacryloxy glycerol; 2-methacryloxy-N-ethyl morpholine; and allyl methacrylate, and the like.

In certain embodiments, the surface modifier is selected from poly(($C_1$-$C_6$) alkyl) acrylate, a poly(($C_1$-$C_6$) alkyl) methacrylate, and a copolymer of poly(($C_1$-$C_6$) alkyl) acrylate and poly(($C_1$-$C_6$) alkyl) methacrylate. In embodiments, a ratio of the surface modifier to halide-containing magnesium compound is from 1:10 to 2:1 wt % or from 1:5 to 1:1 wt %.

Examples of polymer surfactants that are commercially available include those under the trade designation VISCOPLEX® available from RohMax Additives, GmbH, including those having product designations 1-254, 1-256 and those under the trade designations CARBOPOL® and PEMULEN® available from Noveon/Lubrizol.

The polymer surfactant is typically added in a mixture with an organic solvent. When added as a mixture with an organic solvent, the weight ratio of surfactant to organic solvent is from about 1:20 to about 2:1. In another embodiment, the weight ratio of surfactant to organic solvent is from about 1:10 to about 1:1. In yet another embodiment, the weight ratio of surfactant to organic solvent is from about 1:4 to about 1:2.

Treatment with the second titanium compound may include adding the second titanium halide compound and the second electron donor to a solution containing the precipitate to form a solid catalyst composition, and then bringing a temperature of the solid catalyst composition to from 80° C. to 150° C. and further treating with the second titanium compound to form the solid catalyst component. In one embodiment, the treatment may include more than one second electron donor. For example, a plurality of electron donors can be used during treatment with the second titanium compound. In another embodiment, the second titanium compound treatment includes the steps of filtering out the precipitate, adding the second titanium compound and the second electron donor in a solvent to the precipitate to form a solid catalyst composition, and bringing a temperature of the solid catalyst composition to from 80° C. to 150° C. In another embodiment, the second titanium compound treatment includes the steps of adding the second titanium compound to a solution containing the precipitate; and then bringing a temperature of the solid catalyst composition to from 80° C. to 150° C. and further treating with the second titanium compound and the second electron donor to form the solid catalyst component.

Treatment with the second titanium compound may include adding the second titanium halide compound and the second electron donor to a solution containing the precipitate to form a solid catalyst composition, and then bringing a temperature of the solid catalyst composition to from 80° C. to 150° C. and further treating with the second titanium compound to form the solid catalyst component. In another embodiment, the second titanium compound treatment includes the steps of filtering out the precipitate, adding the second titanium compound and the second electron donor in a solvent to the precipitate to form a solid catalyst composition, and bringing a temperature of the solid catalyst composition to from 80° C. to 150° C. In another embodiment, the second titanium compound treatment includes the steps of adding the second titanium compound to a solution containing the precipitate; and then bringing a temperature of the solid catalyst composition to from 80° C. to 150° C. and further treating with the second titanium compound and the second electron donor to form the solid catalyst component.

During this treatment, the supportive electron donor partly or fully is removed from the catalyst component and the electron donors adjust the coordination to magnesium halides resulting in increased catalyst activity.

In one embodiment, for instance, a solid catalyst component can be made in accordance with the present disclosure by combining a magnesium halide, such as magnesium chloride with an epoxy compound. The epoxy compound, for instance, can be epichlorohydrin. The magnesium halide and the epoxy compound can be combined together at a molar ratio of from about 0.5:1 to about 1:0.5, such as from about 0.8:1.2 to about 1.2:0.8. In one embodiment, for instance, the magnesium halide and the epoxy compound can be combined together in approximately a 1 to 1 molar ratio. The magnesium halide and epoxy compound can be combined together in the presence of a phosphate such as tributyl phosphate and a solvent such as toluene. In addition, an aluminum alkoxide surfactant may be present, such as aluminum alkoxide/isopropoxide.

A monoester, such as ethylbenzoate and a silicate, such as tetraethylorthosilicate can be added to the above composition in addition to a titanium halide such as titaniumtetrachloride to cause a precipitate to form. In one embodiment, complexes of the magnesium halide with the monoester, the titanium chloride can form including $Cl_3$—Ti—O—CH$(CH_2Cl)_2$.

The above precipitate can then be treated with a second internal donor, such as an aryl diester and optionally in the presence with a titanium halide. The resulting solid catalyst component can be washed and used as desired.

In general, the resulting solid catalyst component contains a magnesium halide, a titanium halide, the first internal donor or supportive donor, and the second internal donor. In addition, the solid catalyst component can contain residual amounts of an aluminum alkoxide, the organosilicon compound and the phosphorus compound. For example, the amount of the aluminum alkoxide and/or the organosilicon compound present in the final catalyst can be generally greater than about 0.001% by weight, such as greater than about 0.01% by weight, such as greater than about 0.1% by weight and generally less than about 1% by weight, such as less than about 0.5% by weight, such as less than about 0.3% by weight. The solid catalyst component can also contain the phosphorous compound generally in an amount greater than about 0.1% by weight, such as in an amount greater than about 0.2% by weight, such as in an amount greater than about 0.3% by weight, and generally less than about 1% by weight, such as less than about 0.5% by weight.

In an alternative embodiment, especially in order to form spherical particles, the first internal electron donor may include not only a monoester but also a dialkyl ether. In addition, the first internal electron donor can be combined into the catalyst composition with a spherical-promoting surfactant, such as an acrylate surfactant. In one embodiment, for instance, the surfactant may comprise a polyalkyl methacrylate.

The solid catalyst component of the present disclosure is produced with many beneficial properties and characteristics. For instance, in one embodiment, the catalyst component can be made with a relatively high surface area. For example, the BET surface area of the catalyst can be greater than about 100 m²/g, such as greater than about 200 m²/g, such as greater than about 300 m²/g, such as greater than about 400 m²/g and generally less than about 700 m²/g, such as less than about 600 m²/g.

The catalyst system may contain at least one organoaluminum compound in addition to the solid catalyst component. Compounds having at least one aluminum-carbon bond in the molecule can be used as the organoaluminum compound. Examples of organoaluminum compounds include those of Formula:

$$AlR_nX_{3-n}$$

wherein, R independently represents a hydrocarbon group usually having 1 to about 20 carbon atoms, X represents a halogen atom, and 0<n≤3.

Specific examples of the organoaluminum compounds include, but are not limited to, trialkyl aluminums such as triethyl aluminum, tributyl aluminum and trihexyl aluminum; trialkenyl aluminums such as triisoprenyl aluminum; dialkyl aluminum halides such as diethyl aluminum chloride, dibutyl aluminum chloride and diethyl aluminum bromide; alkyl aluminum sesquihalides such as ethyl aluminum sesquichloride, butyl aluminum sesquichloride and ethyl aluminum sesquibromide; alkyl aluminum dihalides such as ethyl aluminum dichloride, propyl aluminum dichloride and butyl aluminum dibromide; dialkyl aluminum hydrides such as diethyl aluminum hydride and dibutyl aluminum hydride; and other partially hydrogenated alkyl aluminum such as ethyl aluminum dihydride, and propyl aluminum dihydride.

The organoaluminum compound can be used in the catalyst system in an amount that the mole ratio of aluminum to titanium (from the solid catalyst component) is from about 5 to about 1. In another embodiment, the mole ratio of aluminum to titanium in the catalyst system is from about 10 to about 700. In yet another embodiment, the mole ratio of aluminum to titanium in the catalyst system is from about 25 to about 400.

The catalyst system may contain one or more selectivity control agents (SCA) in addition to the solid catalyst component. In one embodiment, the selectivity control agent can comprise one or more organosilicon compounds, such as one or more silane compounds. This organosilicon compound can also function as an external electron donor. The organosilicon compound contains silicon having at least one hydrogen ligand (hydrocarbon group). General examples of hydrocarbon groups include alkyl groups, cycloalkyl groups, (cycloalkyl)methylene groups, alkene groups, aromatic groups, and the like.

The organosilicon compound, when used as an external electron donor serving as one component of a Ziegler-Natta catalyst system for olefin polymerization, contributes to the ability to obtain a polymer (at least a portion of which is polyolefin) having a controllable molecular weight distribution and controllable crystallinity while retaining high performance with respect to catalytic activity.

The organosilicon compound is used in the catalyst system in an amount such that the mole ratio of the organoaluminum compound to the organosilicon compound is from about 2 to about 90. In another embodiment, the mole ratio of the organoaluminum compound to the organosilicon compound is from about 5 to about 70. In yet another embodiment, the mole ration of the organoaluminum compound to the organosilicon compound is from about 7 to about 35.

In one embodiment, the organosilicon compound is represented by Formula:

$$R_n—Si(OR')_{4-n}$$

wherein each R and R' independently represent a hydrocarbon group, and n is 0≤n<4.

Specific examples of the organosilicon compound include, but are not limited to trimethylmethoxysilane, trimethylethoxysilane, dimethyldimethoxysilane, dimethyldiethoxysilane, diisopropyldimethoxysilane, diisobutyldimethoxysilane, t-butylmethyldimethoxysilane, t-butylmethyldiethoxysilane, t-amylmethyldiethoxysilane, dicyclopentyldimethoxysilane, diphenyldimethoxysilane, phenylmethyldimethoxysilane, diphenyldiethoxysilane, bis-o-tolydimethoxysilane, bis-m-tolydimethoxysilane, bis-p-tolydimethoxysilane, bis-p-tolydiethoxysilane, bisethylphenyldimethoxysilane, dicyclohexyldimethoxysilane, cyclohexylmethyldimethoxysilane, cyclohexylmethyldiethoxysilane, ethyltrimethoxysilane, ethyltriethoxysilane, vinyltrimethoxysilane, methyltrimethoxysilane, n-propyltriethoxysilane, decyltrimethoxysilane, decyltriethoxysilane, phenyltrimethoxysilane, γ-chloropropyltrimethoxysilane, methyltriethoxysilane, ethyltriethoxysilane, vinyltriethoxysilane, t-butyltriethoxysilane, nbutyltriethoxysilane, iso-butyltriethoxysilane, phenyltriethoxysilane, γ-amniopropyltriethoxysilane, cholotriethoxysilane, ethyltriisopropoxysilane, vinyltributoxysilane, cyclohexyltrimethoxysilane, cyclohexyltriethoxysilane, 2-norbornanetrimethoxysilane, 2-norboranetriethoxysilane, 2-norboranemethyldimethoxysilane, ethyl silicate, butyl silicate, trimethylphenoxysilane, and methyltriallyloxysilane.

In another embodiment, the organosilicon compound is represented by Formula:

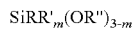

$SiRR'_m(OR'')_{3-m}$ wherein, $0 \leq m < 3$, such as $0 \leq m < 2$; and R independently represents a cyclic hydrocarbon or substituted cyclic hydrocarbon group. Specific examples of the group R include, but are not limited to cyclopropyl; cyclobutyl; cyclopentyl; 2-methylcyclopentyl; 3-methylcyclopentyl; 2-ethylcyclopentyl; 3-propylcyclopentyl; 3-isopropylcyclopentyl; 3-butylcyclopentyl; 3-tertiary-butyl cyclopentyl; 2,2-dimethylcyclopentyl; 2,3-dimethylcyclopentyl; 2,5-dimethylcyclopentyl; 2,2,5-trimethylcyclopentyl; 2,3,4,5-tetramethylcyclopentyl; 2,2,5,5-tetramethylcyclopentyl; 1-cyclopentylpropyl; 1-methyl-1-cyclopentylethyl; cyclopentenyl; 2-cyclopentenyl; 3-cyclopentenyl; 2-methyl-1-cyclopentenyl; 2-methyl-3-cyclopentenyl; 3-methyl-3-cyclopentenyl; 2-ethyl-3-cyclopentenyl; 2,2-dimethyl-3-cyclopentenyl; 2,5-dimethyl-3-cyclopentenyl; 2,3,4,5-tetramethyl-3-cyclopentenyl; 2,2,5,5-tetramethyl-3-cyclopentenyl; 1,3-cyclopentadienyl; 2,4-cyclopentadienyl; 1,4-cyclopentadienyl; 2-methyl-1,3-cyclopentadienyl; 2-methyl-2,4-cyclopentadienyl; 3-methyl-2,4-cyclopentadienyl; 2-ethyl-2,4-cyclopentadienyl; 2,2-dimethyl-2,4-cyclopentadienyl; 2,3-dimethyl-2,4-cyclopentadienyl; 2,5-dimethyl-2,4-cyclopentadienyl; 2,3,4,5-tetramethyl-2,4-cyclopentadienyl; indenyl; 2-methylindenyl; 2-ethylindenyl; 2-indenyl; 1-methyl-2-indenyl; 1,3-dimethyl-2-indenyl; indanyl; 2-methylindanyl; 2-indanyl; 1,3-dimethyl-2-indanyl; 4,5,6, 7-tetrahydroindenyl; 4,5, 6, 7-tetrahydro-2-indenyl; 4,5,6, 7-tetrahydro-1-methyl-2-indenyl; 4,5,6, 7-tetrahydro-1,3-dimethyl-2-indenyl; fluorenyl groups; cyclohexyl; methylcyclohexyl; ethylcylcohexyl; propylcyclohexyl; isopropylcyclohexyl; n-butylcyclohexyl; tertiary-butyl cyclohexyl; dimethylcyclohexyl; and trimethylcyclohexyl.

In the Formula: $SiRR'_m(OR'')_{3-m}$, R' and R'' are identical or different and each represents a hydrocarbon. Examples of R' and R'' are alkyl, cycloalkyl, aryl and aralkyl groups having 3 or more carbon atoms. Furthermore, R and R' may be bridged by an alkyl group, etc. General examples of organosilicon compounds are those of formula (VIII) in which R is cyclopentyl group, R' is an alkyl group such as methyl or cyclopentyl group, and R'' is an alkyl group, particularly a methyl or ethyl group.

Specific examples of organosilicon compounds of Formula $SiRR'_m(OR'')_{3-m}$ include, but are not limited to trialkoxysilanes such as cyclopropyltrimethoxysilane, cyclobutyltrimethoxysilane, cyclopentyltrimethoxysilane, 2-methylcyclopentyltrimethoxysilane, 2,3-dimethylcyclopentyltrimethoxysilane, 2,5-dimethylcyclopentyltrimethoxysilane, cyclopentyltriethoxysilane, cyclopentenyltrimethoxysilane, 3-cyclopentenyltrimethoxysilane, 2,4-cyclopentadienyltrimethoxysilane, indenyltrimethoxysilane and fluorenyltrimethoxysilane; dialkoxysilanes such as dicyclopentyldimethoxysilane, bis(2-methylcyclopentyl)dimethoxysilane, bis(3-tertiary-butylcyclopentyl)dimethoxysilane, bis(2,3-dimethylcyclopentyl)dimethoxysilane, bis(2,5-dimethylcyclopentyl)dimethoxysilane, dicyclopentyldiethoxysilane, dicyclobutyldiethoxysilane, cyclopropylcyclobutyldiethoxysilane, dicyclopentenyldimethoxysilane, di(3-cyclopentenyl)dimethoxysilane, bis(2,5-dimethyl-3-cyclopentenyl)dimethoxysilane, di-2,4-cyclopentadienyl)dimethoxysilane, bis(2,5-dimethyl-2,4-cyclopentadienyl)dimethoxysilane, bis(1-methyl-1-cyclopentylethyl)dimethoxysilane, cyclopentylcyclopentenyldimethoxysilane, cyclopentylcyclopentadienyldimethoxysilane, diindenyldimethoxysilane, bis(1,3-dimethyl-2-indenyl)dimethoxysilane, cyclopentadienylindenyldimethoxysilane, difluorenyldimethoxysilane, cyclopentylfluorenyldimethoxysilane and indenylfluorenyldimethoxysilane; monoalkoxysilanes such as tricyclopentylmethoxysilane, tricyclopentenylmethoxysilane, tricyclopentadienylmethoxysilane, tricyclopentylethoxysilane, dicyclopentylmethylmethoxysilane, dicyclopentylethylmethoxysilane, dicyclopentylmethylethoxysilane, cyclopentyldimethylmethoxysilane, cyclopentyldiethylmethoxysilane, cyclopentyldimethylethoxysilane, bis(2,5-dimethylcyclopentyl)cyclopentylmethoxysilane, dicyclopentylcyclopentenylmethoxysilane, dicyclopentylcyclopentenadienylmethoxysilane and diindenylcyclopentylmethoxysilane; and ethylenebis-cyclopentyldimethoxysilane.

In one embodiment, one or more selectivity control agents are present in the catalyst system. Particularly preferred selectivity control agents include dimethyldimethoxysilane, n-propyltrimethoxysilane, methylcyclohexyldimethoxysilane, diisopropyldimethoxysilane, n-propyltriethoxysilane, bis(perhydroisoquinolino) dimethoxysilane, 2,2,6,6-tetramethylpiperidine, or mixtures thereof.

In one embodiment, one or more selectivity control agents may be used in conjunction with an activity limiting agent (ALA). The activity limiting agent can be an aliphatic ester. The aliphatic ester may be a $C_4$-$C_3$, aliphatic acid ester, may be a mono- or a poly-(two or more) ester, may be straight chain or branched, may be saturated or unsaturated, and any combination thereof. The $C_4$-$C_{30}$ aliphatic acid ester may also be substituted with one or more Group 14, 15 or 16 heteroatom containing substituents. Nonlimiting examples of suitable $C_4$-$C_{30}$ aliphatic acid esters include $C_{1-20}$ alkyl esters of aliphatic $C_{4-30}$ monocarboxylic acids, $C_{1-20}$ alkyl esters of aliphatic $C_{8-20}$ monocarboxylic acids, $C_{1-4}$ allyl mono- and diesters of aliphatic $C_{4-20}$ monocarboxylic acids and dicarboxylic acids, $C_{1-4}$ alkyl esters of aliphatic $C_{5-20}$ monocarboxylic acids and dicarboxylic acids, and $C_{4-20}$ alkyl mono- or polycarboxylate derivatives of $C_{2-10}$, (poly) glycols or $C_{2-100}$ (poly)glycol ethers. In a further embodiment, the $C_4$-$C_{30}$ aliphatic acid ester may be isopropyl myristate, di-n-butyl sebacate, (poly)(alkylene glycol) mono- or diacetates, (poly)(alkylene glycol) mono- or dimyristates, (poly)(alkylene glycol) mono- or di-laurates, (poly)(alkylene glycol) mono- or di-oleates, glyceryl tri (acetate), glyceryl tri-ester of $C_{2-40}$ aliphatic carboxylic acids, and mixtures thereof. In a further embodiment, the $C_4$-$C_{30}$ aliphatic ester is isopropyl myristate or di-n-butyl sebacate.

In one embodiment, the ALA is a non-ester composition. As used herein, a "non-ester composition" is an atom, molecule, or compound that is free of an ester functional group. In other words, the "non-ester composition" does not contain the following functional group

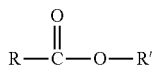

In one embodiment, the non-ester composition may be a dialkyl diether compound or an amine compound. The dialkyl diether compound can be represented by the following formula,

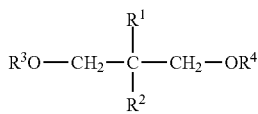

wherein $R^1R^4$ are independently of one another an alkyl, aryl or aralkyl group having up to 20 carbon atoms, which may optionally contain a group 14, 15, 16, or 17 heteroatom, provided that R' and $R^2$ may be a hydrogen atom. Nonlimiting examples of suitable dialkyl ether compounds include dimethyl ether, diethyl ether, dibutyl ether, methyl ethyl ether, methyl butyl ether, methyl cyclohexyl ether, 2,2-dimethyl-1,3-dimethoxypropane, 2,2-diethyl-1,3-dimethoxypropane, 2,2-di-n-butyl-1,3-dimethoxy propane, 2,2-di-isobutyl-1,3-dimethoxy propane, 2-ethyl-2-n-butyl-1,3-dimethoxypropane, 2-n-propyl-2-cyclopentyl-1,3-dimethoxypropane, 2,2-dimethyl-1,3-diethoxypropane, 2-isopropyl-2-isobutyl-1,3-dimethoxypropane, 2,2-dicyclopentyl-1,3-dimethoxypropane, 2-n-propyl-2-cyclohexyl-1,3-diethoxypropane, and 9,9-bis(methoxymethyl)fluorene. In a further embodiment, the dialkyl ether compound is 2,2-diisobutyl-1,3-dimethoxypropane.

In one embodiment, the non-ester composition is an amine compound. Nonlimiting examples of suitable amine compounds include 2,6-substituted piperidines such as 2,6-dimethylpiperidine and 2,2,6,6-tetramethylpiperidine and 2,5-substituted piperidines. In a further embodiment, the piperidine compound is 2,2,6,6-tetramethylpiperidine.

For ALA's that contains more than one carboxylate groups, all the carboxylate groups are considered effective components. For example, a sebacate molecule contains two carboxylate functional groups is considered to have two effective functional molecules.

As described above, in one embodiment, the activity limiting agent is a C4 to C30 Aliphatic acid ester. Alternatively, the activity limiting agent may comprise a diether or a poly(alkene glycol) ester of a C4 to C30 aliphatic acid. Particular activity limiting agents that may be incorporated into the catalyst system include isopropyl myristate, di-n-butyl sebacate, ethyl 4-ethoxybenzoate, propoxylated (POE) coco fatty acid esters such as containing 10 to 20 mols of POE, a poly(ethylene)glycol coco fatty acid ester, or mixtures thereof.

An especially preferred combination of SCA/ALA components is a mixture of an alkoxy silane selected from the group consisting of dicyclopentyldimethoxysilane, methylcyclohexyl-dimethoxysilane, and n-propyltrimethoxysilane with an ester which is isopropyl myristate, di(n-butyl) sebacate, (poly)(ethylene glycol) monolaurate, (poly)alkene glycol) dioleate, (poly)(ethylene glycol) methyl ether laurate, glyceryl tri(acetate), or a mixture thereof.

Preferred SCA/ALA mixtures according to the invention are those comprising from 1 to 99.9, more preferably from 30 to 99, and most preferably from 50 to 98 equivalent percent of one or more ALA compounds, and correspondingly from 99 to 0.1, more preferably from 70 to 1, most preferably from 50 to 2 equivalent percent of one or more alkoxysilane compounds. Regardless of the foregoing range of components, it is to be understood by the skilled artisan that the normalized polymerization activity at an elevated temperature should be less than that obtainable at 67° C. and less than that obtainable if the alkoxysilane alone were employed alone in the same total SCA molar amount.

The total molar quantity of the SCA mixture employed in the present invention based on moles of transition metal is desirably from 0.1 to 500, more desirably from 0.5 to 100 and most preferably from 1.0 to 50 With respect to quantity of ALA, the corresponding molar ratio based on transition metal is desirably from 1 to 10,000, preferably from 2 to 1000, and most preferably from 5 to 100.

Catalyst particle morphology is indicative of the polymer particle morphology produced therefrom. The three parameters of polymer particle morphology (sphericity, symmetry and aspect ratio) may be determined using a Camsizer instrument marketed by Horiba Scientific. Camsizer Characteristics:

Sphericity $$SPHT = \frac{4\pi A}{P^2} = \text{Circularity2 (ISO 9276-6)},$$

where:
P is the measured perimeter/circumference of a particle projection; and
A is the measured area covered by a particle projection.
P is the measured perimeter/circumference of a particle projection; and
A is the measured area covered by a particle projection.
For an ideal sphere, SPHT is defined as 1. Otherwise, the value is less than 1.
The symmetry is defined as:

$$Symm_{0,3} = \frac{1}{2}\left(1 + \min\left(\frac{r_1}{r_2}\right)\right)$$

where, $r_1$ und $r_2$ are distance from the centre of area to the borders in the measuring direction. For asymmetric particles Symm is less than 1. If the centre of the area is outside the particle, i.e.

$$\frac{r_1}{r_2} < 0,$$

the Symm is less than 0.5
$x_{Ma}=r_1+r_2$, or "Symm," is the minimum value of measured set of symmetry values from different directions.

Aspect Ratio:

$$b/l_{0,2,3} = \frac{x_{c\ min}}{x_{Fe\ max}}$$

where $x_{c\ min}$ and $X_{Fe\ max}$ out of the measured set of $x_c$ and $x_{Fe}$ values.

The catalyst morphology characteristics such as aspect ratio ("B/L3") can be used for characterization of polymer morphology. In some processes, the aspect ratio is higher than 0.6, or higher than 0.7, or higher than 0.8, or higher than 0.90.

The particle size of the resulting catalyst component can vary depending upon the process conditions and the desired result. In general, the $D_{50}$ particle size can be greater than about 5 microns, such as greater than about 10 microns, such as greater than about 20 microns, such as greater than about 30 microns, such as greater than about 40 microns, such as greater than about 50 microns, such as greater than about 60 microns, and generally less than about 70 microns, such as less than about 50 microns, such as less than about 30 microns, such as less than about 25 microns.

Polymerization Processes

Polymerization of olefins can be carried out in the presence of the catalyst systems as prepared and described above. Various different olefins can be polymerized in accordance with the present disclosure. For example, catalyst systems of the present disclosure can be used to polymerize ethylene, propylene, and the like. The catalyst systems can also be used to produce homopolymers and copolymers. Generally speaking, an olefin monomer, such as propylene, is contacted with the catalyst system described above under suitable conditions to form desired polymer products. In one embodiment, preliminary polymerization described below is carried out before the main polymerization. In another embodiment, polymerization is carried out without preliminary polymerization. In yet another embodiment, the formation of a polypropylene-co-polymer is carried out using at least two polymerization zones.

Of particular advantage, the catalyst component of the present disclosure is well suited for use in all different types of polymerization processes. For instance, the catalyst component of the present disclosure can be used in bulk loop polymerization processes, gas phase processes, and the like. The catalyst component can also be used in a slurry process.

In preliminary polymerization, the solid catalyst component is usually employed in combination with at least a portion of the organoaluminum compound. This may be carried out in the presence of part or the whole of the organosilicon compound (external electron donor compound). The concentration of the catalyst system used in the preliminary polymerization may be much higher than that in the reaction system of the main polymerization.

In preliminary polymerization, the concentration of the solid catalyst component in the preliminary polymerization is usually from about 0.01 to about 200 millimoles, or from about 0.05 to about 100 millimoles, calculated as titanium atoms per liter of an inert hydrocarbon medium described below. In one embodiment, the preliminary polymerization is carried out by adding propylene or a mixture of propylene with another olefin and the above catalyst system ingredients to an inert hydrocarbon medium and polymerizing the olefins under mild conditions.

Specific examples of the inert hydrocarbon medium include, but are not limited to aliphatic hydrocarbons such as propane, butane, pentane, hexane, heptanes, octane, decane, dodecane and kerosene; alicyclic hydrocarbons such as cyclopentane, cyclohexane and methylcyclopentane; aromatic hydrocarbons such as benzene, toluene and xylene; and mixtures thereof. In certain embodiments, a liquid olefin may be used in place of part or the whole of the inert hydrocarbon medium.

The olefin used in the preliminary polymerization may be the same as, or different from, an olefin to be used in the main polymerization.

The reaction temperature for the preliminary polymerization is sufficient for the resulting preliminary polymer to not substantially dissolve in the inert hydrocarbon medium. In one embodiment, the temperature is from about −20° C. to about 100° C. In another embodiment, the temperature is from about −10° C. to about 80° C. In yet another embodiment, the temperature is from about 0° C. to about 40° C.

Optionally, a molecular-weight controlling agent, such as hydrogen, may be used in the preliminary polymerization. The molecular weight controlling agent is used in such an amount that the polymer obtained by the preliminary polymerization has an intrinsic viscosity, measured in decaliter at 135° C., of at least about 0.2 dl/g, or from about 0.5 to 10 dl/g.

In one embodiment, the preliminary polymerization is carried out so that from about 0.1 g to about 1,000 g of a polymer is formed per gram of the solid catalyst component of the catalyst system. In another embodiment, the preliminary polymerization is carried out so that from about 0.3 g to about 500 g of a polymer is formed per gram of the solid catalyst component. If the amount of the polymer formed by the preliminary polymerization is too large, the efficiency of producing the olefin polymer in the main polymerization may sometimes decrease, and when the resulting olefin polymer is molded into a film or another article, fish eyes tend to occur in the molded article. The preliminary polymerization may be carried out batchwise or continuously.

After the preliminary polymerization conducted as above, or without performing any preliminary polymerization, the main polymerization of the propylene is carried out in the presence of the above-described polymerization catalyst system formed from the solid catalyst component, the organoaluminum compound and the organosilicon compound (external electron donor compound).

Examples of other olefins that can be used in the main polymerization with propylene are α-olefins having 2 to 20 carbon atoms such as ethylene, propylene, 1-butene, 4-methyl-1-pentene, 1-pentene, 1-octene, 1-hexene, 3-methyl-1-pentene, 3-methyl-1-butene, 1-decene, 1-tetradecene, 1-eicosene, and vinylcyclohexane. In illustrative processes, these α-olefins may be used individually or in any combination.

In one embodiment, propylene is homopolymerized, or a mixed olefin containing propylene as a main component is copolymerized. When the mixed olefin is used, the proportion of propylene as the main component is usually at least about 50 mole %, or at least about 70 mole %.

By performing the preliminary polymerization, the catalyst system in the main polymerization can be adjusted in the degree of activity. This adjustment tends to result in a powdery polymer having a high bulk density. Furthermore, when the preliminary polymerization is carried out, the particles shape of the resulting polymer becomes spherical, and in the case of slurry polymerization, the slurry attains excellent characteristics while in the case of gas phase polymerization, the polymer seed bed attains excellent characteristics. Furthermore, in these embodiments, a polymer having a high stereoregularity index can be produced with a high catalytic efficiency by polymerizing an α-olefin having at least 3 carbon atoms. Accordingly, when producing the propylene copolymer, the resulting copolymer powder or the copolymer becomes easy to handle.

In the copolymerization of the propylene, a polyunsaturated compound such as conjugated diene or non-conjugated diene may be used as a comonomer. Examples of comonomers include styrene, butadiene, acrylonitrile, acrylamide, α-methyl styrene, chlorostyrene, vinyl toluene, divinyl benzene, diallyphthalate, alkyl methacrylates and alkyl acrylates. In one embodiment, the comonomers include thermoplastic and elastomeric monomers. The main polymerization of an olefin is carried out usually in the gaseous or liquid phase. In one embodiment, polymerization (main polymerization) employs a catalyst system containing the solid catalyst component in an amount from about 0.001 to about 0.75 millimoles calculated as Ti atom per liter of the volume of the polymerization zone, the organoaluminum compound in an amount from about 1 to about 2,000 moles per mole of titanium atoms in the solid catalyst component, and the organosilicon compound in an amount from about 0.001 to about 10 moles calculated as Si atoms in the organosilicon compound per mole of the metal atoms in the organoaluminum compound. In another embodiment, polymerization employs a catalyst system containing the solid catalyst component in an amount of from 0.005 to about 0.5 milimoles calculated as Ti atom per liter of the volume of the polymerization zone, the organoaluminum compound in an amount from about 5 to about 500 moles per mole of titanium atoms in the solid catalyst component, and the organosilicon compound in an amount from about 0.01 to about 2 moles calculated as Si atoms in the organosilicon compound per mole of the metal atoms in the organoaluminum compound. In yet another embodiment, polymerization employs a catalyst system containing the alkyl benzoate derivative in an amount from about 0.005 to about 1 mole calculated as Si atoms in the organosilicon compound per mole of the metal atoms in the organoaluminum compound.

When the organoaluminum compound and the organosilicon compound are used partially in the preliminary polymerization, the catalyst system subjected to the preliminary polymerization is used together with the remainder of the catalyst system components. The catalyst system subjected to the preliminary polymerization may contain the preliminary polymerization product.

The use of hydrogen at the time of polymerization promotes and contributes to control of the molecular weight of the resulting polymer, and the polymer obtained may have a high melt flow rate. In this case, the stereoregularity index of the resulting polymer and the activity of the catalyst system can be increased according to the above methods.

In one embodiment, the polymerization temperature is from about 20° C. to about 170° C. In another embodiment, the polymerization temperature is from about 50° C. to about 165° C. In one embodiment, the polymerization pressure is typically from atmospheric pressure to about 100 kg/cm². In another embodiment, the polymerization pressure is typically from about 2 kg/cm² to about 50 kg/cm². The main polymerization may be carried out batchwise, semi-continuously or continuously. The polymerization may also be carried out in two or more stages under different reaction conditions.

The olefin polymer so obtained may be a homopolymer, a random copolymer, a block copolymer or an impact copolymer. The impact copolymer contains an intimate mixture of a polyolefin homopolymer and a polyolefin rubber. Examples of polyolefin rubbers include ethylene propylene rubber (EPR) such as ethylene propylene methylene copolymer rubber (EPM) and ethylene propylene diene methylene terpolymer rubber (EPDM).

The olefin polymer obtained by using the catalyst system has a very small amount of an amorphous polymer component and therefore a small amount of a hydrocarbon-soluble component. Accordingly, a film molded from the resultant polymer has low surface tackiness.

The polyolefin obtained by the polymerization process is excellent in particle size distribution, particle diameter and bulk density, and the copolyolefin obtained has a narrow composition distribution. In an impact copolymer, excellent fluidity, low temperature resistance, and a desired balance between stiffness and elasticity can be obtained.

In one embodiment, propylene and an α-olefin having 2 or from about 4 to about 20 carbon atoms are copolymerized in the presence of the catalyst system described above. The catalyst system may be one subjected to the preliminary polymerization described above. In another embodiment, propylene and an ethylene rubber are formed in two reactors coupled in series to form an impact polymer.

The α-olefin having 2 carbon atoms is ethylene, and examples of the α-olefin having about 4 to about 20 carbon atoms are 1-butene, 1-pentene, 4-methyl-1-pentene, 1-octene, 1-hexene, 3-methyl-1-pentene, 3-methyl-1-butene, 1-decene, vinylcyclohexane, 1-tetradecene, and the like.

In the main polymerization, propylene may be copolymerized with two or more such α-olefins. For example, it is possible to copolymerize propylene with ethylene and 1-butene. In one embodiment, propylene is copolymerized with ethylene, 1-butene or ethylene and 1-butene.

Copolymerization of propylene and another α-olefin may be carried out in two stages. The polymerization in a first stage may be the homopolymerization of propylene or the copolymerization of propylene with the other α-olefin. In one embodiment, the amount of the monomers polymerized in the first stage is from about 50 to about 95% by weight. In another embodiment, the amount of the monomers polymerized in the first stage is from about 60 to about 90% by weight. This first stage polymerization may be carried out in two or more stages under the same or different polymerization conditions.

In one embodiment, the polymerization in a second stage is carried out such that the mole ratio of propylene to the other α-olefin(s) is from about 10/90 to about 90/10. In another embodiment, the polymerization in a second stage is carried out such that the mole ratio of propylene to the other α-olefin(s) is from about 20/80 to about 80/20. In yet another embodiment, the polymerization in a second stage is carried out such that the mole ratio of propylene to the other α-olefin(s) is from about 30/70 to about 70/30. Producing a crystalline polymer or copolymer of another α-olefin may be provided in the second polymerization stage.

The propylene copolymer so obtained may be a random copolymer or the above described block copolymer. The propylene copolymer can contain from about 7 to about 50 mole % of units derived from the α-olefin having 2 or from about 4 to about 20 carbon atoms. In one embodiment, a propylene random copolymer contains from about 7 to about 20 mole % of units derived from the α-olefin having 2 or from about 4 to about 20 carbon atoms. In another embodiment, the propylene block copolymer contains from about 10 to about 50 mole % of units derived from the α-olefin having 2 or 4-20 carbon atoms.

In another embodiment, copolymers made with the catalyst system contain from about 50% to about 99% by weight poly-α-olefins and from about 1% to about 50% by weight comonomers (such as thermoplastic or elastomeric monomers). In another embodiment, copolymers made with the catalyst system contain from about 75% to about 98% by weight poly-α-olefins and from about 2% to about 25% by weight comonomers.

In one embodiment, a two stage reactor system, such as two fluidized bed reactors in series, can be used to produce a polypropylene copolymer that is heterophasic. For example, in one embodiment, a polypropylene homopolymer or polypropylene random copolymer of a first phase is prepared in a first stage reactor. The first phase can comprise a continuous polymer phase in the resulting polymer. An elastomeric propylene copolymer is then produced in a second stage and forms the second phase. The first stage polymerization can be carried out in one or more bulk reactors or in one or more gas phase reactors. The second stage polymerization can be carried out in one or more gas phase reactors. The second stage polymerization is typically carried out directly following the first stage polymerization. The resulting heterophasic copolymer, which can comprise a propylene-ethylene copolymer, can have excellent impact resistance properties and have elastomeric properties.

The catalyst as described above is particularly well suited for use in producing polypropylene polymers in two stage reactors. The catalyst, for instance, has been found to have a dramatically prolonged lifetime and therefore maintains high catalyst activity levels within the second reactor. It is believed that the increased lifetime of a catalyst helps to produce polymer resins with better flow properties.

In one embodiment, the catalyst efficiency (measured as kilogram of polymer produced per gram of catalyst) of the catalyst system is at least about 30 kg/g/h. The catalyst deficiency, for instance, can be higher than about 60 kg/g/h, such as greater than about 80 kg/g/h, such as greater than about 100 kg/g/h, such as greater than about 140 kg/g/h.

The catalysts/methods discussed above can in some instances lead to the production of poly-α-olefins having melt flow rates ("MFR", g/10 minutes) from about 0.01 to about 500 g/10 min, such as from about 0.1 to about 400 g/10 min. In another embodiment, poly-α-olefins having an MFR from 0.1 to about 300 are produced.

In addition to the melt flow rate, the polydispersity index (PI) can vary depending upon various factors and the desired result. The polydispersity index can generally be greater than about 3, such as greater than about 5, and generally less than about 8, such as less than about 6.

The catalysts/methods described above can in some instances lead to the production of poly-α-olefins having bulk densities (BD) of at least about 0.35 cc/g. In another embodiment, poly-α-olefins having a BD of at least about 0.4 cc/g are produced. In one embodiment, for instance, polypropylene polymers can be produced having a relatively high bulk density. The bulk density, for instance, can be greater than 0.415 g/cm$^3$, such as greater than 0.42 g/cm$^3$, such as greater than 0.44 g/cm$^{3'}$ such as greater than 0.46 g/cm$^3$. The bulk density is generally less than about 0.8 g/cm$^3$, such as less than about 0.6 g/cm$^3$.

The catalysts/methods described above can lead to the production of poly-α-olefins having a Span of less than 1.0. In some embodiments, the Span is less than 0.6.

Embodiments of the present invention can lead to the production of a propylene block copolymer and impact copolymers including polypropylene based impact copolymer having one or more excellent melt-flowability, moldability, desirable balance between rigidity and elasticity, good stereospecific control, good control over polymer particle size, shape, size distribution, and molecular weight distribution, and impact strength with a high catalytic efficiency and/or good operability. Employing the catalyst systems containing the solid catalyst component according to embodiments of the present invention yields catalysts simultaneously having high catalytic efficiency, and one or more of excellent melt-flowability, extrudability, moldability, rigidity, elasticity and impact strength.

The following examples illustrate embodiments of the present invention. Unless otherwise indicated in the following examples and elsewhere in the specification and claims, all parts and percentages are by weight, all temperatures are in degrees Celsius, and pressure is at or near atmospheric.

EXAMPLES

Abbreviations and Definitions

"$D_{10}$" represents the size of particles (diameter), wherein 10% of particles are less than that size, "$D_{50}$" represents the size of particles, wherein 50% of particles are less than that size, and "$D_{90}$" represents the size of particles, wherein 90% of particles are less than that size. "Span" represents the distribution of the particle sizes of the particles. The value can be calculated according to the following formula:

$$\text{Span}=(D_{90}-D_{10})D_{50}$$

"PP" prior to any D or Span value indicates the D value or Span value for polypropylene prepared using the catalysts indicated unless otherwise specified, all values are in microns.

BD is an abbreviation for bulk density, and is reported in units of g/ml or g/cm$^3$. To measure bulk density, the polymer is dried in an oven at 60° C. for one hour and then cooled to room temperature before measurement. A cylindrical measuring cup is used that is 9½ inches in height and has an inside diameter of 1.8 inches. The measuring cup has a volume of 395 ml. A funnel having a 1 inch diameter opening at the bottom is mounted 1½ inches above the measuring cup. The small end of the funnel is covered with a straight edge. 500 ml of polymer sample is loaded into the funnel. The straight edge is then quickly removed which allows the polymer sample to flow into the measuring cup. Immediately after flow of the polymer into the cup has stopped, a straight edge is used to remove excess sample from the top of the measuring cup. The bulk density is equal to the net sample mass divided by 395 ml.

CE is an abbreviation for catalyst efficiency and is reported in units of Kg polymer per gram of catalyst (Kg/g) during the polymerization for 1 hour.

MFR is an abbreviation for melt flow rate and is reported in units of g/10 min. The MFR is measured according to ASTM test number D1238 at 230° C. with a 2.16 kg load.

The catalyst component particle size analysis was conducted using laser light scattering method by Malvern Mastersizer 3000 instrument. Toluene used as a solvent.

The surface area and pore size distribution of the catalyst components were measured by Micrometrics ASAP 2020 instrument. The catalyst component samples were degassed by heating at 60° C. under vacuum for few hours before the measurement.

The polydispersity index (PI) and zero shear viscosity for polymer samples were obtained from rheological data by ARES G2 Rheometer. The stabilized polymer sample is pressed on hot press to make plate. The polymer plate is then analyzed on the Rheometer. From the data plot PI and zero shear viscosity are calculated using built in MWD software.

The Cup Test is a method to measure polymer powder flowability. The test is particularly well suited to measuring the flowability of high rubber content polypropylene impact copolymers. The test is especially useful when polymer resins are sticky making angle of repose measurements unreliable. The method includes filling a polystyrene 12 oz. coffee cup with the polymer resin powder. The cup is filled with the polymer resin and a flat edge is used to remove excess. The cup is then inverted on a flat surface for 30 minutes. The cup is then removed and a tester observes the shape of the powder and how long it takes to deform and collapse from the initial cup shape. The Cup Test can be measured in seconds for the powder to collapse. The Cup Test also includes a Cup Test Index as specified below:

| Cup Test Index | Powder Shape Retention Time |
|---|---|
| 0 | Immediately loses its shape |
| 1 | 1 second to lose its shape |
| 2 | 15 seconds to lose its shape |
| 3 | 1 minute to lose iths shape |
| 4 | Indefinite-needs some agitation to lose its shape |
| 5 | Indefinite-needs considerable agitation to make it lose its shape |
| 6 | Indefinite-needs aggressive agitation to make it lose its shape |
| 7 | Never |

NPDE is an abbreviation for a non-phthalate diaryl ester and can be of the formula:

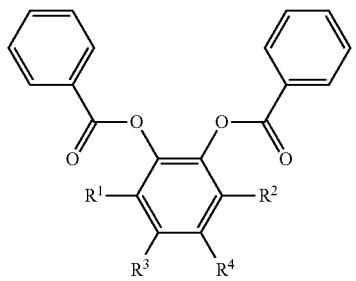

where $R^1$-R4-selected from substituted or unsubstituted aryl groups, $R^3R^4R^5R^6$ are the same or different alkyl or cycloalkyl having 1 to 20 carbon atoms, heteroatom or combination of them. As used herein, NPDE1 is 3-methyl-5-tert-butyl-1,2-phenylene dibenzoate. NPDE2, on the other hand, is described in paragraph 52 of U.S. Patent Publication US 2013/0261273, which is incorporated herein by reference.

SYLTHERM is a tradename for a polydimethyl siloxane (PDMS) that is commercially available from Dow Chemical.

VISCOPLEX is a tradename for a polyalkyl methacrylate available from Evonik.

EB is an abbreviation for ethyl benzoate.

TBP is an abbreviation for tributyl phosphate.

ECH is an abbreviation for epichlorohydrin.

TEOS is an abbreviation for tetraethylorthosilicate.

Ti, Mg, and D are the weight percentages (wt %) for each of the titanium, magnesium, and internal donor (NPDE), respectively, in the composition.

XS is an abbreviation for xylene solubles, and is reported in units of wt %.

Bulk Propylene Polymerization

Where catalysts of the examples are used in a method of propylene polymerization the following method was used. The reactor was baked at 100° C. under nitrogen flow for 30 minutes prior to the polymerization run. The reactor was cooled to 30-35° C. and cocatalyst (1.5 ml of 25 wt % triethylaluminum (TEA1)), C-donor [cyclohexylmethydimethoxysilane] (1 ml), hydrogen (3.5 psi) and liquid propylene (1500 ml) were added in this sequence into the reactor. The catalyst (5-10 mg), loaded as a mineral oil slurry, was pushed into the reactors using high pressure nitrogen. The polymerization was performed for one hour at 70° C. After the polymerization, the reactors were cooled to 22° C., vented to atmospheric pressure, and the polymer collected.

Gas Phase Propylene Polymerization

Where catalysts of the examples are used in a method of propylene polymerization the following method was used. The reactor was baked at 100° C. under nitrogen flow for 30 minutes prior to the polymerization run. The reactor was cooled to 30° C. and propylene was charged (120 g), with cocatalyst (0.27 ml of 25 wt % triethylaluminum (TEA1)), C-donor [cyclohexylmethydimethoxysilane] (0.38 ml), and hydrogen (0.5 g). A reactor was heated to 35° C. and the catalyst component (0.5-0.7 mg) was flashed to the reactor with propylene (120 g). The polymerization was performed for one hour at 70° C. After the polymerization, the reactors were cooled to 22° C., vented to atmospheric pressure, and the polymer collected.

Examples 1-3 illustrates preparing the catalyst components using an organosilicon compound without supportive donor and provides the properties of polymer produced using a bulk propylene polymerization scheme.

Example 1 demonstrates preparing the catalyst component using tetraethylorthosilicate. The catalyst produced polymer with raspberry shape particle morphology with BD below 0.40 g/cc and B/L3<0.7

3.3 g of $MgCl_2$, 20 g toluene, 6.7 g TBP, 6.43 g of ECH was charged to reactor. The mixture was heated to 60° C. and held for 8 hours at 600 RPM agitation speed. The mixture was allowed to cool to 25°. 27 grams of toluene and 1.5 grams of tetraethylorthosilicate in 3 grams toluene were added to the reactor at 25° C. The reactor was cooled to −25° C. and 65.2 grams of $TiCl_4$ was added. After the addition, the stirring rate was dropped to 200 rpm and the reaction was heated to 35° C. for over two hours and held for 30 minutes, heated to 85° C. for 30 minutes and held for 30 minutes. Filter. The reaction was washed with 50 mL of toluene, 3×. 65 ml of toluene was added and the reactor was heated to 40° C. @ 400 RPM. 0.64 grams of NPDE1 was added and the reactor was heated up to 105° C. and held for one hour. Filter. 65 mL of 10% $TiCl_4$ was added and the temperature raised to 105° C. for one hour. Filter. 65 mL of 10% $TiCl_4$ was added and the temperature raised to 110° C. for 30 minutes and filtered 3 times. The solid was washed with 50 mL of hexanes @ 65° C. and 400 RPM 3 times. The catalyst component was discharged as a hexane slurry. The analytical data and the catalyst performance is presented below.

Example 2 demonstrates the catalyst component using two organosilicon compounds (tetraethylorthosilicate and Syltherm PDMS) and Al(OiPr)3. The internal donor was added in two places: in before the solid formed and to the solid component. The catalyst produced polymer with rounded raspberry type morphology and improved bulk density (BD=0.44 g/cc).

3.3 g of $MgCl_2$ to correct subscript, 0.25 g Al(O-iPr)3, 20 g toluene, 9.1 g TBP, 1.0 g Syltherm(PDMS), 3.55 g of ECH was charged to reactor. The mixture was heated to 60° C. and held for 8 hours at 600 RPM agitation speed. The mixture was allowed to cool to 25° C. 27 grams of toluene, 1.5 grams of TEOS in 3 grams of toluene, and 0.64 grams of NPDE1 were added the reactor. The reactor was chilled to -25° C. and 65.4 grams of $TiCl_4$ was added to the reactor. The agitation was set to 300 RPM and ramped to 35° C. over 2 hours. The reaction was held at 35° C. for 30 minutes @ 300 RPM. The reaction was heated to 85° C. and held for 30 minutes. The reaction was filtered and 50 mL of toluene was added. The reactor was heated to 40° C. @ 400 RPM and 0.64 grams of NPDE1 was added. The reactor continued heating to 105° C. and was held for 1 hour, then allowed to settle and decanted. 65 mL of 10% $TiCl_4$ was added, heated to 105° C. and held for 1 hour. The reaction was allowed to settle and it was decanted. 65 mL of 10% $TiCl_4$ was added, heated to 110° C. and held for 1 hour. The reaction was allowed to settle and it was decanted. 50 mL of hexane was added and stirred for 5 minutes @ jacket temperature of 65° C. The reaction was allowed to settle and was decanted. Hexane was then added and the product was discharged as a hexane slurry.

Example 3 demonstrates the catalyst component using two organosilicon compounds (tetraethylorthosilicate and Syltherm PDMS) and Al(OiPr)3. The internal donor was added to the solid component. The particle size of catalyst component increased to 14 microns (compared with examples 1 and 2).

3.3 g of $MgCl_2$, 0.25 g Al(O-iPr)3, 20 g toluene, 6.7 g TBP, 1.0 g Syltherm(PDMS), 6.43 g of ECH was charged to the reactor. The mixture was heated to 60° C. and held for 8 hours @ 600 RPM agitation speed. The mixture was allowed to cool to 25° C. 27 grams of toluene, 1.5 grams of TEOS in 3 grams of toluene were added to reactor at 600 rpm and 25° C. The reactor was cooled to -25° C. and 65.2 grams of $TiCl_4$ was added. The reactor was heated to 35° C. @ 200 RPM for over two hours and held at 35° C. for 30 minutes; heated to 85° C. over 30 minutes and held at 85° C. for 30 minutes and decanted washed 3× with toluene. Cool to 25° C. and let sit over weekend. Filter, add 65 mL of toluene. Heat to 40° C. @ 400 RPM and add 0.64 grams NPDE1. Heat to 105° C. for one hour. Filter. Add 65 mL of 10% $TiCl_4$, heat to 105° C., hold for one hour. Filter. Add 65 mL of 10% $TiCl_4$, heat to 110° C., hold for one hour. Filter. Wash with 50 mL of hexanes 3×, jacket temperature @ 65, agitate 5 minutes between washes. Discharge as hexane slurry.

Example 4 (Comparative)

This example demonstrates preparing the catalyst component without organosilicon compound. The catalyst produced polymer with irregular morphology with agglomerated polymer particles.

3.3 g of $MgCl_2$, 1.15 g Al(O-iPr)3, 20 g toluene, 6.7 g TBP, 6.43 g of ECH was charged to reactor 14A. The mixture was heated to 60° C. and held for 8 hours @ 600 RPM agitation speed. The mixture was allowed to cool to 25° C. 30 grams of toluene was added to the reactor at 25° C. and 600 RPM. The reactor was cooled to -25° C. and 65.2 grams of $TiCl_4$ was added. After the addition, the stirring rate was dropped to 200 and the reaction was heated to 35° C. over two hours. Hold for 30 minutes. Heated to 85° C. for 30 minutes. Hold for 30 minutes. Filter. The reaction was washed with 50 mL of toluene, 3×, JT 80° C., 400 RPM. Filter. 65 ml of toluene was added and the reactor was heated to 40° C. @ 400 RPM. 0.64 grams NPDE1 was added and the reactor was heated up to 105° C. and held for one hour. Filter. 65 mL of 10% $TiCl_4$ was added and the temperature raised to 105° C. for one hour. Filter. 65 mL of 10% $TiCl_4$ was added and the temperature raised to 110° C. for 30 minutes and filtered 3 times. The reactor was washed with 50 mL of hexanes @ 65° C. and 400 RPM 3 times. The product was discharged as a hexane slurry.

TABLE 1

Catalyst components prepared with two organosilicon compounds and Al(OiPr)3

| Example | Component Present | D10 | D50 | D90 | Span | Ti % | Mg % | NPDE1 % |
|---|---|---|---|---|---|---|---|---|
| Example 1 | TEOS | 5.81 | 9.84 | 14.9 | 0.928 | 3.79 | 17.34 | 9.83 |
| Example 2 | Al(OiPr)3, Syltherm, TEOS, NPDE1 | 5.02 | 8.94 | 13.8 | 0.982 | 3.94 | 15.76 | 17.08 |
| Example 3. | Al(OiPr)3, Syltherm, TEOS, | 9.67 | 14.5 | 21.5 | 0.817 | 4.19 | 17.64 | 9.73 |
| Example 4 (comparative) | Al—O only | 3.85 | 7.12 | 13.5 | 1.356 | 2.818 | 18.48 | 7.41 |

TABLE 2

Catalysts and polymer properties (catalyst components prepared with two organosilicon compounds and Al(OiPr)3)

| Catalyst component | CE kg/g | MFR, g/10 min | XS, % | BD, g/cm³ | PP D10 | PP D50 | PP D90 | PP Span | B/L3 | Comment on PP morphology |
|---|---|---|---|---|---|---|---|---|---|---|
| Example 1 | 65 | 1.46 | 3.1 | 0.397 | 353 | 590 | 1120 | 1.3 | 0.66 | Raspberry shape |
| Example 2 | 91.2 | 0.25 | 1.88 | 0.443 | 319 | 495 | 915 | 1.204 | 0.681 | Rounded raspberry shape |

TABLE 2-continued

Catalysts and polymer properties (catalyst components prepared with two organosilicon compounds and Al(OiPr)3)

| Catalyst component | CE kg/g | MFR, g/10 min | XS, % | BD, g/cm$^3$ | PP D10 | PP D50 | PP D90 | PP Span | B/L3 | Comment on PP morphology |
|---|---|---|---|---|---|---|---|---|---|---|
| Example 3 | 54.4 | 1.84 | 2.22 | 0.394 | 319 | 617 | 1081 | 1.235 | 0.682 | Grape shape |
| Example 4 (comparative) | 51.4 | 2.86 | 4.07 | 0.237 | 612 | 1393 | 2085 | 1.057 | 0.624 | Irregular morphology |

Examples 5-13 illustrate preparing the catalyst components using a supportive donor, ethyl benzoate. (EB)

TABLE 3

Catalyst components prepared with organosilicon compounds and with supportive donors

| Example | Comments | D10 (μ) | D50 (μ) | D90 (μ) | Span | Ti % | Mg % | NPDE1, % |
|---|---|---|---|---|---|---|---|---|
| Example 5 (Comparative) | No epoxy compound | 6.0 | 10.5 | 18.3 | 1.173 | 3.6 | 16.16 | 16.17 |
| Example 6 | Syltherm/TEOS = 2/1; EB/MgCl$_2$ = 0.34 | 14.9 | 24.0 | 37.2 | 0.929 | 3.36 | 17.62 | 13.5 |
| Example 7 | Syltherm/TEOS = 1/1; EB/MgCl$_2$ = 0.34 | 9.4 | 18.0 | 26.6 | 0.960 | 3.26 | 15.21 | 11.7 |
| Example 8 | TEOS; EB/MgCl$_2$ = 0.34 | 12.7 | 18.6 | 26.1 | 0.720 | 3.71 | 16.37 | 14.2 |
| Example 9 | Syltherm/TEOS = 1/2; EB/MgCl$_2$ = 0.34 | 8.7 | 14.1 | 19.8 | 0.788 | 3.53 | 16.25 | 11.7 |
| Example 10 | Syltherm; EB/MgCl$_2$ = 0.34 | 3.1 | 10.5 | 17.2 | 1.338 | 2.96 | 16.4 | 11.3 |
| Example 11 | TEOS; EB/MgCl$_2$ = 0.26, rpm 300 | 6.4 | 10.2 | 14.9 | 0.842 | 3.16 | 17.36 | 10.4 |
| Example 12 | TEOS; EB/MgCl$_2$ = 0.26, rpm 200 | 8.6 | 13.6 | 20.7 | .889 | 3.01 | 8.56 | 10.9 |
| Example 13 | No organosilicon compound, EB | 6.9 | 11.9 | 18.8 | .996 | 3.06 | 7.19 | 11.1 |
| Example 14 (Comparative) | No organosilicon compound, Phthalic anhydride | 9.8 | 20.2 | 33.5 | .173 | 2.52 | 8.70 | 10.46 |

45

TABLE 4

Catalysts and polymer properties (catalyst components prepared with organosilicon compounds and with supportive donors) (bulk propylene polymerization)

| Catalyst Component | CE kg/g | MFR, g/10 min | XS, % | BD, g/ml | PP D50 (μ) | PP Span | B/L3 | PP morphology |
|---|---|---|---|---|---|---|---|---|
| Example 5 (Comparative) | 70.9 | 0.23 | 2.89 | 0.321 | 449 | 1.178 | 0.672 | Irregular, agglomerated small particles |
| Example 6 | 91.7 | 0.10 | 2.29 | 0.383 | 1087 | 0.573 | 0.706 | Rounded raspberry shape |
| Example 7 | 82.9 | 0.26 | 2.28 | 0.418 | 836 | 0.435 | 0.720 | Rounded raspberry shape |
| Example 8 | 81.1 | 0.17 | 2.40 | 0.424 | 899 | 0.433 | 0.738 | Rounded shape |
| Example 9 | 84.3 | 0.17 | 3.14 | 0.454 | 705 | 0.704 | 0.707 | Rounded raspberry shape |
| Example 10 | 83.1 | 0.12 | 2.23 | 0.421 | 970 | 0.992 | 0.625 | Raspberry shape |
| Example 11 | 81.9 | 0.34 | 2.44 | 0.447 | 492 | 0.754 | 0.719 | Rounded shape |
| Example 12 | 79.4 | 0.2 | 2.00 | 0.425 | 643 | 0.736 | 0.713 | Rounded raspberry shape |
| Example 13 (Comparative) | 75.4 | 0.07 | 1.83 | 0.410 | 644 | 0.626 | 0.699 | Grape shape with small subparticles |
| Example 14 (Comparative) | 53.9 | 0.10 | 0.127 | 0.404 | 772 | 0.764 | — | Grape type |

Example 5 (Comparative)

The catalyst component was made using tetraethylorthosilicate and the supportive donor, ethyl benzoate, and without an epoxy compound to dissolve $MgCl_2$. This example demonstrates an irregular polymer morphology with low BD.

$MgCl_2$ (12.0 g) and hexane (130 g) were combined to form an initial reaction mixture. To the mixture was then added 2-ethylhexanol (50 g) with stirring (600 rpm), and the temperature was then raised to 120° C. This temperature was then maintained for 4 hours. To the reaction mixture was then added tetraethylorthosilicate (1.75 g in 2.0 g of hexane), and the reaction was held for 20 minutes, followed by cooling to −25° C. At the low temperature, $TiCl_4$ (150 ml) was added over 1.5 hours, after which time the temperature was raised to room temperature. At room temperature ethyl benzoate (2 g in 2 g hexane) was added and the mixture heated to 100° C. A NPDE1 (3.0 g in 5 g of toluene) was then added and the reaction mixture maintained at 100° C. for 1 hour. The solid material was then collected by filtration and it was washed with toluene (3×200 mL at 85° C. with 10 minute stirrings at temperature before re-filtration). Upon re-suspending the solid in toluene, additional NPDE1 (2.0 g in 5.0 g of toluene) was added at 40° C., and the solid collected by filtration and washed with hexane. The process of adding NPDE1, heating at 110° C. (0.5 hours) and filtering was then repeated process of washing with hexane and filtering was then repeated 3 times. Finally, the solid product was washed with (4×300 ml hexane at 65° C.), and the solid discharged to a hexane slurry.

FIG. 1 is a photograph of the polymer obtained from Example 5 (Comparative). The images presented are SEM images of polypropylene particles produced with the catalysts from the corresponding examples. Because the polymer particles replicate the catalyst particles, we can compare the catalyst morphology in each example. The catalyst and polymer morphology are key factors to consider in commercial polymer production processes. The polymerization processes require good flowability of the polymer for transfer of the polymer from one reactor unit to another. The process should operate without producing any polymer fines that result in a plugging polymerization reactor. Therefore, for any polymerization process the strong and uniform morphology of the catalyst and high bulk density of polymer is preferred.

As illustrated in FIG. 1, the polymer morphology of polymer prepared by Example 5 (Comparative) includes small sub-particles. The bulk density of polymer is very low at 0.321 g/ml. The catalyst and polymer from this example are not favored and would result in the plugging reactor by the fines that are generated.

Example 6

Granular supported catalyst component prepared with Syltherm and TEOS (as organosilicon compounds) and ethyl benzoate as supportive electron donor. The example demonstrates improvement of the catalyst component with larger particle size 24 microns and high activity catalyst (catalyst efficiency 92 kg/g) and producing polymer with rounded shape.

$MgCl_2$ (13.2 g), $Al(OCH(CH3)2)3$ (1.0 g), toluene (59.5 g), tri-n-butylphosphate (36.3 g), epichlorohydrin (14.25 g), and Syltherm (6.0 g) are combined and heated to 60° C. with agitation at 600 rpm for 8 hours under a nitrogen atmosphere. Upon cooling to room temperature, toluene (140 g) was added, along with ethyl benzoate (4.5 g) and tetraethylorthosilicate (3 g). The mixture was then cooled to −25° C. and $TiCl_4$ (261 g) was slowly added under 600 rpm stirring, while maintaining the temperature at −25° C. After the addition was complete, the temperature was maintained for 1 hour prior to warming to 35° C. over 30 minutes, at which temperature it was held for 30 minutes, then the temperature was raised to 85° C. over 30 minutes, and held for 30 minutes prior to collection of a solid precipitate via filtration. The solid precipitate was washed three times with toluene (200 ml, each wash).

Figure 2:
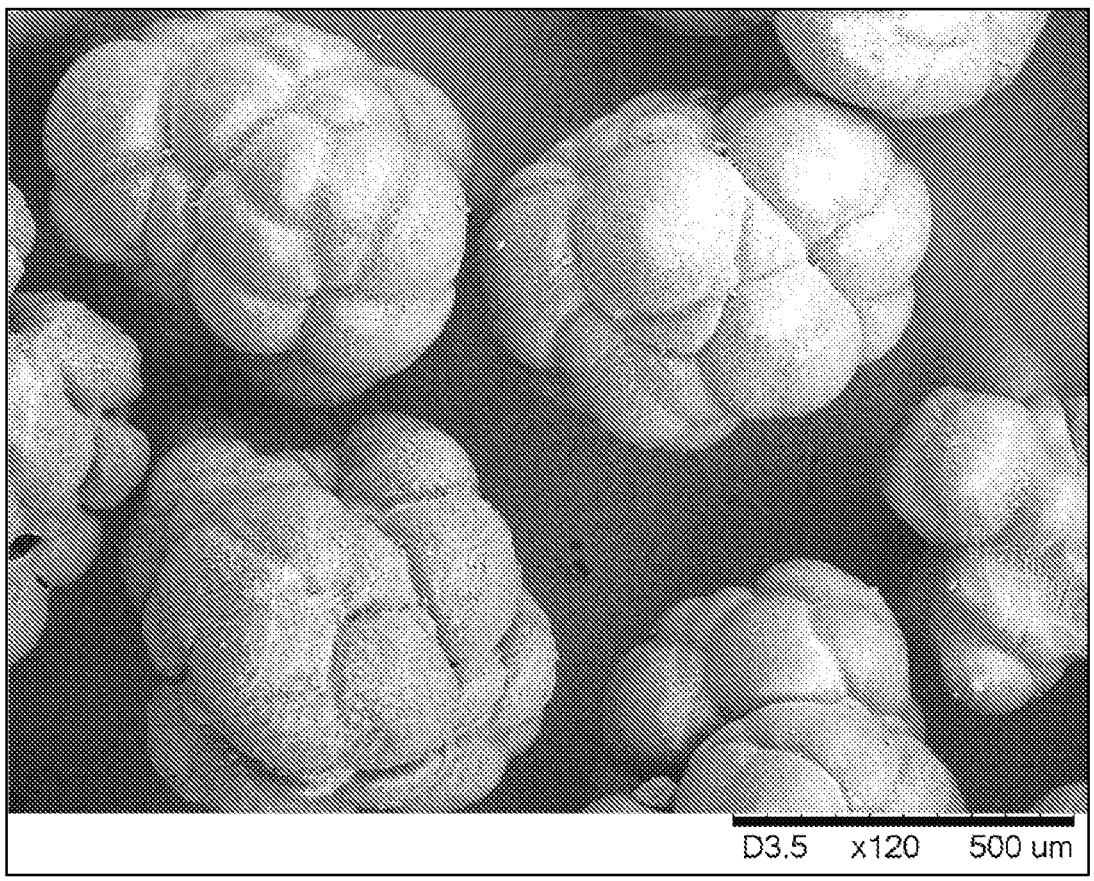
FIG. 2 shows a microscopic view of the polymer produced with the catalyst component of Example 7.

The resulting precipitate was then combined with $TiCl_4$ in toluene (264 ml; 10 vol %). This mixture was heated under agitation to 85° C., followed by addition of NPDE 1 (2.0 g) in toluene (10 g). Heating at 85° C. was continued for 1 hour prior to collection of the solid via filtration. This process of combining with $TiCl_4$ in toluene, heating, adding NPDE 1, was repeated at 95° C. and again at 110° C. before washing the final product four times with hexane (200 ml, each wash), and agitating at 60-65° C. for 10 minutes for each wash. The catalyst component was then discharged as a hexane slurry. FIG. 2 is a photograph of the polymer produced with the catalyst component obtained from Example 6. Polymer morphology like rounded raspberry shape with large subparticles.

Example 7

This example produced a granular supported catalyst illustrating high BD catalyst/PP, with a narrow Span. Example 6 was repeated, however the PDMS was added at 3.0 g, and $Al(OCH(CH3)2)3$ (0.5 g) and NPDE 1 (2.0 g) was added in toluene wash before the final $TiCl_4$/Toluene treatment.

Example 8

Example 7 was repeated, however the TEOS was added at 6.0 g and no Syltherm was added. This example produced a granular supported catalyst which produced polymer with rounded shape morphology (B/L3=0.74)

Example 9

Figure 3:
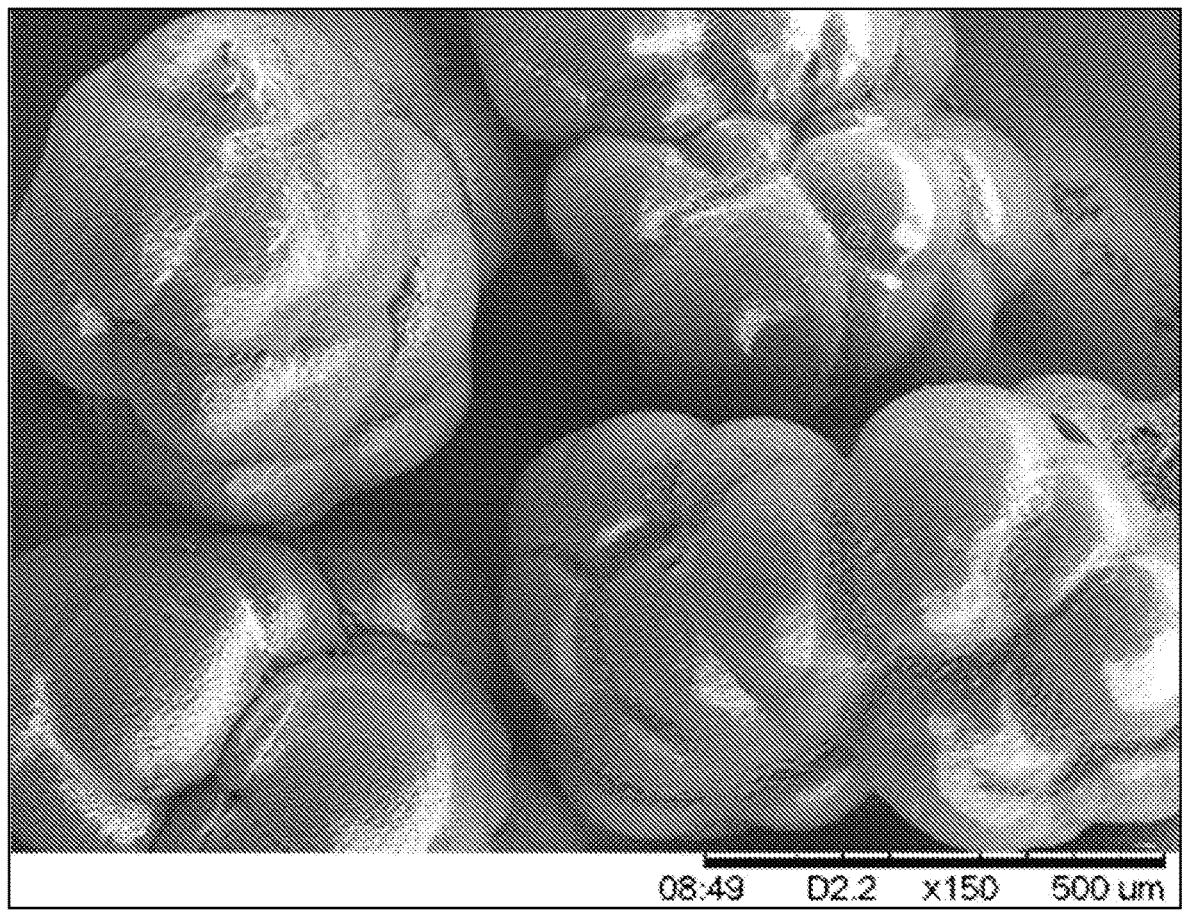
FIG. 3 shows a microscopic view of the polymer produced with the catalyst component of Example 9.

This example produced a granular supported catalyst illustrating improvement of the catalyst and polymer morphology, and showing high BD catalyst/PP, with a narrow Span. The polymer is illustrated in FIG. 3. Example 7 was repeated; however the TEOS was added at 1.50 g.

Example 10

Illustrates preparation of catalyst component using Syltherm as organosilicon silicon compound. Granular supported catalyst component demonstrating reduction of particle sizes. Example 7 was repeated, however no TEOS was added.

FIGS. 2 and 3 illustrate the rounded raspberry type morphology of polymers prepared by the catalysts of Examples 7, and 9, respectively, using an epoxy compound to dissolve $MgCl_2$, along with varying combinations of organosilicon compounds (polydimethoxysilane (PDMS) and tetraethoxysilane (TEOS)), and ethyl benzoate, demonstrate improvement in catalyst and polymer morphology. The FIGS. 2 and 3. show the materials as having a well-defined morphology. The large sub-particles are associated in large particles. The polymers produced with these catalysts exhibit a high density (>0.40 g/ml) and sphericity (B/L3>0.71) (see tables above).

Example 11

Demonstrates effect of amount of supportive donor on catalyst component particle size. Example 8 was repeated except amount of ethyl benzoate was reduced from 0.34 g/gMgCl$_2$ to 0.26 g/gMgCl$_2$ which resulted in a reduction of the catalyst component particle size from 18.6 microns to 10.2 microns.

Figure 4:
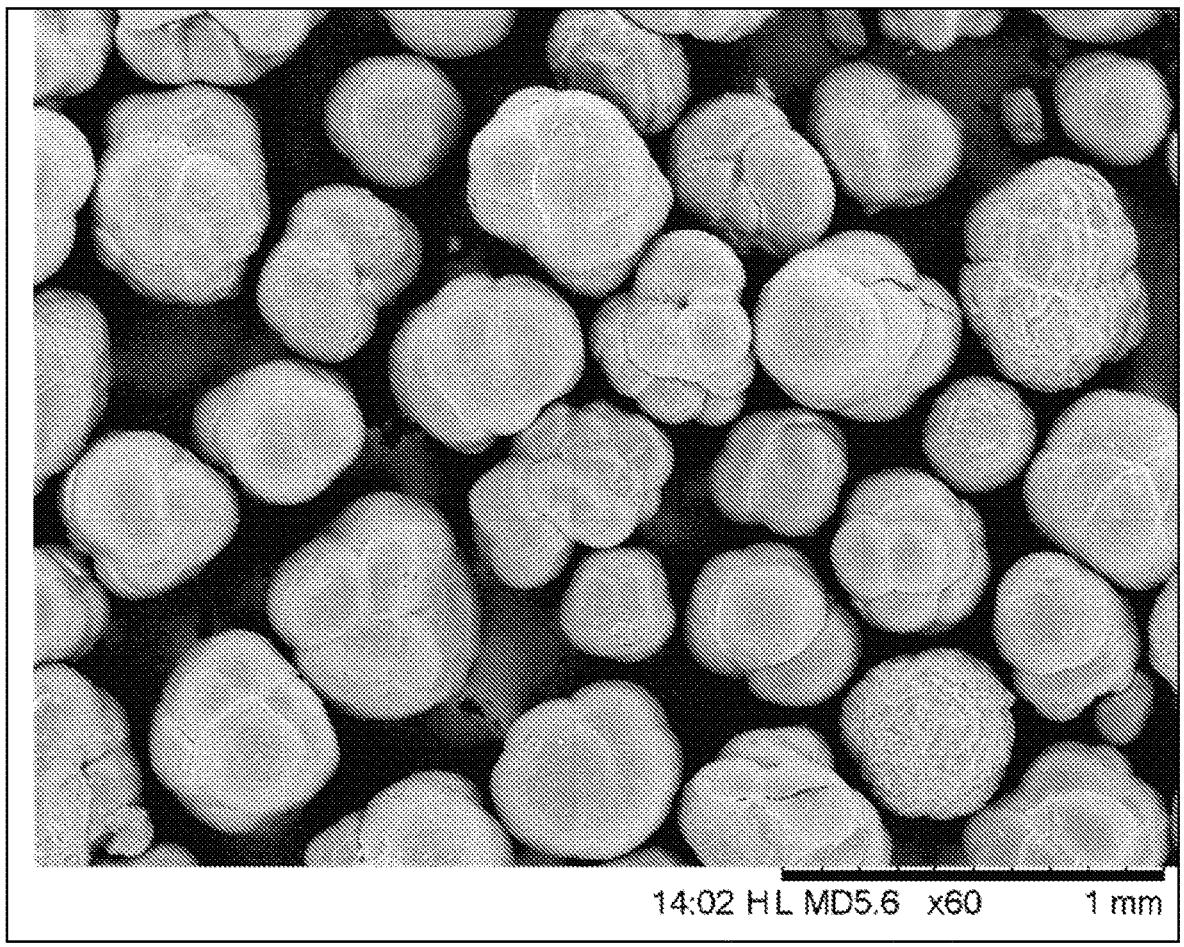
FIG. 4 shows a microscopic view of the polymer produced with the catalyst component of Example 11.

FIG. 4 the rounded shape of polymer morphology produced by the catalyst from Example 11.

Example 12

Demonstrates effect of agitation speed during the precipitation of the catalyst component on catalyst component particle size. Example 11 was repeated except the agitation speed was reduced from 300 rpm to 200 rpm, which resulted in increasing catalyst component particle size from 10.2 microns to 13.6 microns

Example 13. (Comparative)

Figure 5:
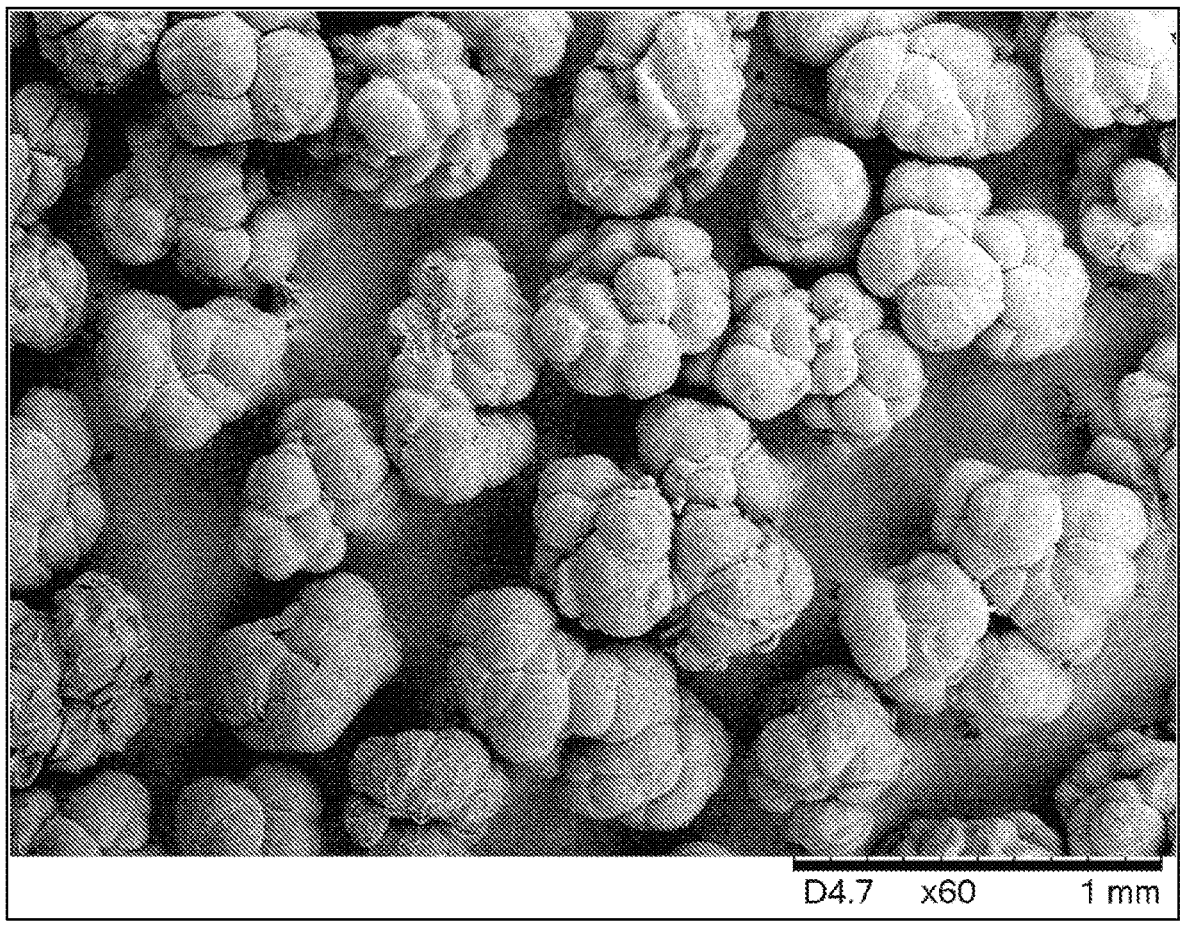
FIG. 5 shows a microscopic view of the polymer produced with the catalyst component of Example 13 (Comparative).

Granular supported catalyst demonstrating reduction of particle sizes and bulk density of the catalyst and polymer. No Al(OCH(CH3)2)3, Syltherm, or TEOS was used. Example 7 was repeated, however no Al(OCH(CH3)2)3, PDMS, or TEOS was added. Example 13 demonstrates that performance of the catalyst component prepared by using an epoxy compound to dissolve the MgCl$_2$, and using only ethyl benzoate as a supportive donor without using organosilicon compounds. FIG. 5 represents the morphology of polymer produced according to Example 13. Each polymer particle contains numerous small sub-particles. In some polymerization processes, this morphology is not favored because these particles can be easily disintegrated up during the polymerization process.

Example 14. (Comparative)

Catalyst component made with phthalic anhydride as a precipitation agent. The catalyst component contains bis(1,3-dichloro-iso-propyl) phthalate (1.2%) and phthaloyl chloride (0.3%) as a reaction product of phthalic anhydride with TiCl$_4$ and Mg-compounds during the catalyst component preparation. The catalyst component shows lower catalyst activity than the catalyst produced under the current claims. The polymer particle morphology is a grape type with B/L3<0.70.

MgCl$_2$ (13.2 g), toluene (190.0 g), tri-n-butylphosphate 26.6 g), ECH (25.6 g) were combined and heated to 60° C. with agitation at 600 rpm for 8 hours under a nitrogen atmosphere. Phthalic anhydride was added (4.6 g) at 60° C. The mixture was then cooled to −25° C., at which temperature TiCl$_4$ (260 g) was slowly added with 600 rpm agitation. The temperature was maintained for 1 hour, followed by raising the temperature to 10° C. over 30 minutes, holding for 30 minutes, raising to 85° C. over 70 minutes, and holding for 15 minutes before collecting the solid via filtration. The solid was washed three times with toluene (200 ml) for 10 minutes each at the 85° C. The solid was then collected by filtration and washed with toluene (265 ml). After filtration, the TiCl$_4$/toluene solution and NPDE 1 (3.0 g) in toluene (2 g), was added and heated at 105° C. After again filtering, the solid was collected, and washed with the TiCl$_4$/toluene solution at 110° C. under agitation. Finally, the solid was washed with hexane (200 ml) four times under agitation at 60-65° C., with the catalyst being discharged as a hexane slurry. The catalyst of Example 14 demonstrates lower catalyst activity than the catalyst prepared without phthalic anhydride.

Examples 15-17 illustrate the catalyst component preparation using TEOS as organosilicon compound and ethyl benzoate as a supportive electron donor. Examples 18-23 illustrate the polymerization data in bulk propylene and gas phase reactors producing polymer with substantially spherical shape.

Example 15

Example of 11 was repeated in a scale of MgCl$_2$=20 kg

Example 16

Add 13.2 g MgCl$_2$, 0.5 g Al(OR)3, 72 g toluene, 25.7 g ECH, 26.8 g TBP, Heat and Agitate at 60 C/600 rpm/8 hr. Cool down to 25 C. Leave for next day under N2 Blanket. Add 75.0 g toluene, 3.5 g EB in 12 g toluene, 6.0 g TEOS in 8 g toluene @ 25 C. Cool to −25 C @ 600 rpm and add 260.8 g TiCl$_4$ slowly addition. Raise from −25 C to 35 C over 2 hr @ 350 rpm and hold at 35 C for 30 min/350 rpm. Raise from 35 C to 85 C in 30 min and hold at 85 C for 30 min @ 350 rpm filter. Wash w/200 ml toluene/3×/10 min & add 200 ml toluene leave under N2 Blanket Next day & Filter. Add 265 ml of Toluene heat, add 1.25 g of NPDE1, heat 105° C. 400 rpm 1 hr. Filter, 1st Act add 265 ml 10% TiCl$_4$/tol heat to 105 C/400 rpm/1 hr and filter From the 2nd Act to 4th Act, add 265 ml 10% TiCl$_4$/tol heat to 110 C/400 rpm/30 minutes and filter Wash w/200 ml of hexane @ 65 C JT/4×/10 min & discharge as hexane slurry

Example 17

Example 15 was repeated with increasing the NPDE1 amount by 10%

TABLE 5

| | Catalyst Component Comment | D10 | D50 | D90 | Span | Ti % | Mg % | NPDE1 % |
|---|---|---|---|---|---|---|---|---|
| Example 15 | TEOS, EB (20 kg of MgCl$_2$ scale) | 8.8 | 11.6 | 15.4 | 0.570 | 3.04 | 16.85 | 10.68 |
| Example 16 | ECH/MgCl$_2$ = 2 (mol); TEOS, EB | 11.5 | 17.5 | 26.4 | 0.851 | 2.95 | 16.88 | 10.54 |
| Example 17 | TEOS, EB (20 kg of MgCl$_2$ scale) | 6.19 | 11.4 | 18.1 | 1.044 | 2.56 | 16.64 | 10.37 |

TABLE 6

| Example | Catalyst Component | Polymerization condition | CE kg/g | MFR, g/10 min | XS, % | BD, g/cm³ | PP D10 | PP D50 | PP D90 | PP Span | B/L3 | PP morphology |
|---|---|---|---|---|---|---|---|---|---|---|---|---|
| Example 18 | From example 15 | Bulk | 70.6 | 1.36 | 2.40 | 0.463 | 490 | 717 | 1698 | 1.685 | 0.706 | Rounded shape |
| Example 19 | From example 15 | Gas Phase | 64.3 | 4.20 | 2.15 | 0.436 | 443 | 511 | 672 | 0.447 | 0.797 | Substantially spherical shape |
| Example 20 | From example 16 | Bulk | 93.6 | 0.26 | 2.25 | 0.432 | 706 | 848 | 1107 | 0.473 | 0.762 | Rounded Shape |
| Example 21 | From example 16 | Gas Phase | 63.9 | 1.70 | 1.94 | 0.389 | 645 | 756 | 919 | 0.363 | 0.782 | Substantially spherical shape |
| Example 22 | From example 17 | Bulk | 90.1 | 0.33 | 2.04 | 0.435 | 446 | 558 | 843 | 0.711 | 0.763 | Substantially spherical shape |
| Example 23 | From example 17 | Gas Phase | 60.6 | 1.4 | 1.89 | 0.414 | 423 | 508 | 716 | 0.575 | 0.763 | Substantially spherical shape |

Figure 6:
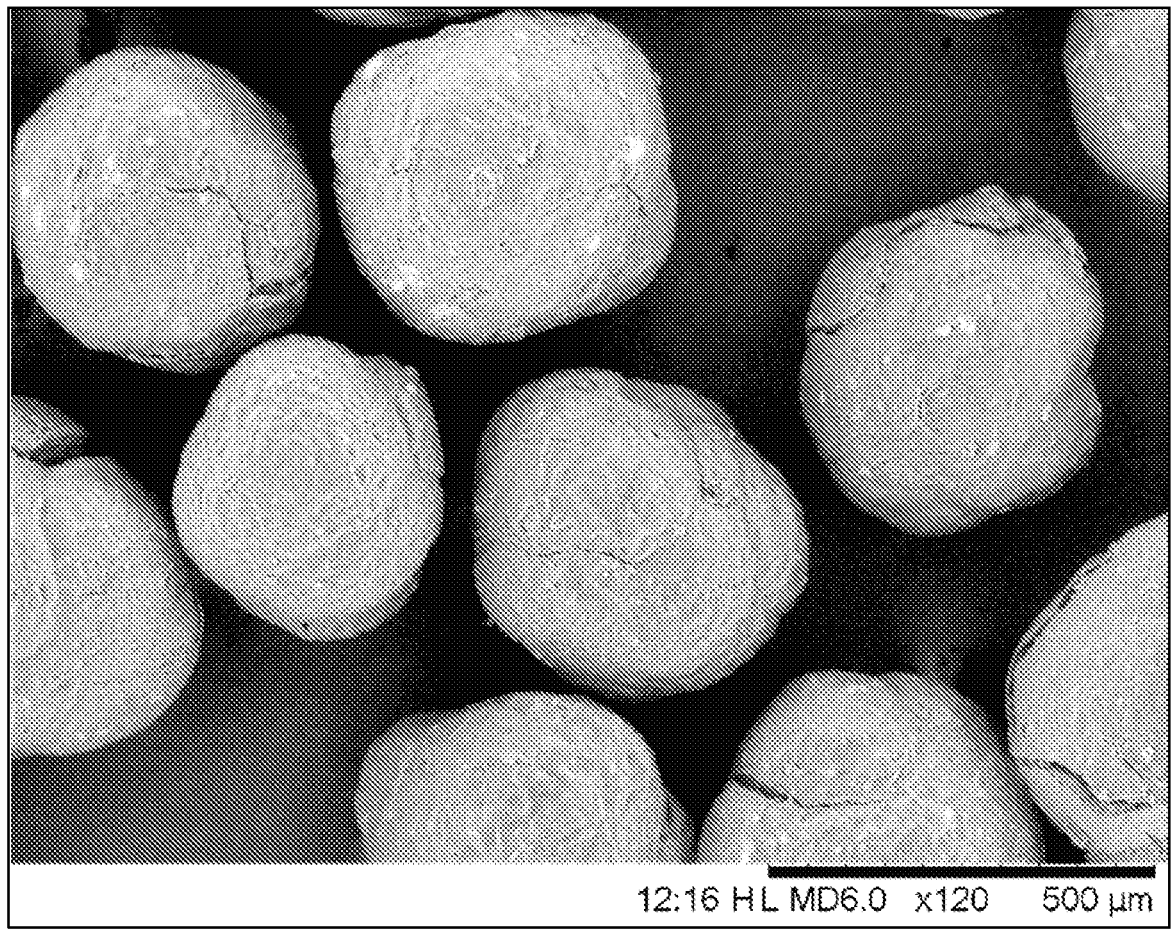
FIG. 6 shows a microscopic view of the polymer produced with the catalyst component of Example 23.

Examples 18-23 demonstrate production polymer in bulk and gas phase polymerization reactors with substantially spherical shape of particles with B/L3 of 0.8. FIG. 6 shows PP with substantially spherical shape morphology (microspheres) from example 23.

Surface area (BET) measurement and porosity of the catalyst components show surface area of around 400 m2/g.

TABLE 7

Surface area (BET)

| Catalyst component | SA, BET, m²/g | Ads PV, cm³/g | Des PV, cm³/g | Ads PD, A | Des PD, A |
|---|---|---|---|---|---|
| Example 23 | 395.0 | 0.2714 | 0.2719 | 27.4841 | 27.5313 |

Examples 24-27 illustrate the relationship of the catalyst performances and relatively ratio of supportive electron donor and internal electron donor. The catalyst isotacticity reduces (% XS) with increasing EB/NPDE1 ratio but the catalyst activity does not change sufficiently.

TABLE 8

Analytical data for catalyst components and corresponding catalyst polymerization data with variable ratio of supportive electron donor and electron donor

| Example | NPDE1/ MgCl2, wt | Ti, % | Mg % | NPDE1, % | EB, % | CE kg/g | MFR, g/10 min | XS, % |
|---|---|---|---|---|---|---|---|---|
| Example 24 | 0.227 | 3.37 | 18.62 | 13.06 | 6.03 | 102.3 | 0.16 | 2.21 |
| Example 25 | 0.182 | 3.37 | 16.93 | 10.70 | 7.46 | 93.7 | 0.14 | 2.53 |
| Example 26 | 0.152 | 3.57 | 17.15 | 9.34 | 8.50 | 91.6 | 0.35 | 3.07 |
| Example 27 | 0.121 | 3.62 | 16.7 | 7.73 | 9.90 | 96.3 | 0.35 | 3.87 |

Catalyst components in Examples 24 through 27 were produced as in Example 8 except the amount of NPDE1 was used as in Table 8. Catalyst component particle sizes are 32 microns (produced with agitation speed of 200 rpm during the support precipitation).

Example 28 illustrates granular catalyst components prepared with NPDE2 as an internal donor diaryl ester and example 29 presents polymerization data in bulk propylene.

Example 28

Example 8 was repeated except NPDE2 was used as internal electron donor (NPDE2/MgCl$_2$=0.18 (wt)

The catalyst component was tested in bulk propylene polymerization to evaluate the hydrogen response on MFR.

TABLE 8

Analytical data for catalyst components with NPDE 2

| | Conditions | D10 | D50 | D90 | Span | Ti % | Mg % | D % |
|---|---|---|---|---|---|---|---|---|
| Example 28 | NPDE2, TEOS | 11.2 | 18.8 | 28.9 | 0.940 | 3.53 | 17.12 | n/a |

TABLE 9

| | Catalyst component | H2, SL | CE kg/g | MFR, g/10 min | XS, % | BD, g/cm³ | PP D10 | PP D50 | PP D90 | PP Span | B/L3 |
|---|---|---|---|---|---|---|---|---|---|---|---|
| Example 29 | From example 28 | 5 | 94.7 | 1.5 | 3.36 | 0.424 | 762 | 986 | 1604 | 0.854 | 0.696 |

As shown above, Example 29 was conducted at a hydrogen concentration of 5 SL. In general, the hydrogen concentration can be from about 5 SL to about to 40 SL or higher. In general, at lower hydrogen concentrations, such as less than about 20 SL, such as less than about 10 SL, polymers are produced having a relatively low melt flow rate. For instance, the melt flow rate can be less than about 8 g/10 min, such as less than about 5 g/10 min, such as less than about 3 g/10 min, such as less than about 2 g/10 min, such as less than 1 g/10 min, and generally greater than about 0.01 g/10 min. At higher hydrogen amounts, such as greater than about 30 SL, such as from about 30 SL to about 50 SL, the melt flow rate can be dramatically increased. For instance, the melt flow rate can be greater than about 100 g/10 min, such as greater than about 150 g/10 min, such as greater than about 200 g/10 min, such as greater than about 250 g/10 min, such as greater than about 300 g/10 min, such as greater than about 350 g/10 min, such as greater than about 400 g/10 min, such as greater than about 450 g/10 min, such as greater than about 500 g/10 min, and generally less than about 800 g/10 min.

Hydrogen concentration can have some impact on catalyst activity. In general, the catalyst activity can range from about 90 kg/g to about 200 kg/g. A catalyst activity of from about 150 kg/g to about 200 kg/g can reflect a flat kinetic profile.

Hydrogen concentration generally does not impact bulk density or particle size. For instance, the bulk density can be greater than about 0.3 g/cc, such as greater than about 0.35 g/cc, such as greater than about 0.4 g/cc, and generally less than about 0.5 g/cc, such as less than about 0.45 g/cc. The D50 particle size can generally be from about 500 microns to about 1700 microns, and generally from about 800 microns to about 1400 microns. The B/L3 of the polymer can generally be greater than about 0.6, such as greater than about 0.65 and generally less than about 0.8, such as less than about 0.75.

Examples 30-32 illustrate preparing the catalyst components using 1,3 diether (3,3-bis(methoxymethyl)-2,6-dimethylheptane) (DEMH) as an internal donor.

Example 30

Added 6.6 g $MgCl_2$, 0.5 g Al(O-iPr)3, 48 g toluene, 18.2 g TBP, 7.1 g ECH to reactor. Heated and agitated at 60° C./600 rpm/8 hr. Cooled down to 25 C. Added 35 g toluene, 2.25 g ethyl benzoate in 5 g toluene, 3.0 g TEOS in 5 g toluene and 0.75 g of DEMH in 5 g of toluene @ 25 C. Cooled to −25 C @ 600 rpm and added 130.4 g $TiCl_4$ slowly addition. Raised from −25 C to 35 C over 2 hr @ 250 rpm and held at 35 C for 30 min/250 rpm. Raised from 35 C to 85 C in 30 min, held for 1 hour and filtered off. Washed w/100 ml toluene/3×/10 min. Added 132 ml of 10% $TiCl_4$/toluene, added (1.25 g of DEMH in 5 g of toluene @ 40 C. heat at 80 C for 1 h, filtered off. Added 132 ml of 10% $TiCl_4$/tol and heated at 105 for 1 hour. The treatment was repeated at 110° C. for 30 min three more times. The solid was washed with hexane and discharged as a hexane slurry.

Example 31

Example 8 was repeated except the solid precipitation was conducted at 350 rpm agitator speed and 0.80 g of DEMH used as an internal donor with 15% $TiCl_4$/toluene treatment.

Example 32

Example 9 was repeated except the catalyst treatment was conducted with 20% $TiCl_4$/toluene.

TABLE 10

Catalyst component characterization (1,3 diether (3,3-bis(methoxymethyl)-2,6-dimethylheptane) (DEMH)

| | D50 | Span | Ti % | Mg % | DEMH, % | CE kg/g | MFR, g/10 min | XS, % | BD, g/cm³ | PP D50 | PP Span | B/L3 | PP morphology |
|---|---|---|---|---|---|---|---|---|---|---|---|---|---|
| Example 30 | 18.4 | 1.014 | | | 19.2 | 76.2 | 8.5 | 1.24 | 0.407 | 835 | 0.620 | 0.736 | Substantially spherical shape |
| Example 31 | 10.8 | 0.525 | 2.66 | 18.03 | 12.2 | 74.6 | 6.8 | | 0.424 | 710 | 1.244 | 0.672 | Rounded raspberry shape |
| Example 32 | 11 | 0.547 | 2.92 | 17.84 | 12.9 | 98.0 | 5.1 | 2.83 | 0.437 | 616 | 1.268 | 0.688 | Rounded raspberry shape |

Example 33

Demonstration of the preparation and performance of the spherical catalyst component. $MgCl_2$ (13.2 g), Al(OCH(CH3)2)3 (1.0 g), toluene (59.5 g), tri-n-butylphosphate ("TBP;" 36.3 g), ECH (14.25 g), and Syltherm (6.0 g) are combined and heated to 60° C. with agitation at 600 rpm for 8 hours under a nitrogen atmosphere. Upon cooling to room temperature hexane (59.0 g), dibutyl ether (8 g in 13 g hexane), Viscoplex (6.0 g) in hexane (40 g), and EB (4.5 g) in hexane (5 g) were mixed and cooled to 0° C., at which temperature $TiCl_4$ (288 g) was slowly added with 600 rpm agitation. The temperature was maintained for 1 hour, followed by raising the temperature to 10° C. over 30 minutes, holding for 30 minutes, raising to 85° C. over 70 minutes, and holding for 15 minutes before collecting the solid via filtration. The solid was washed three times with toluene (200 ml) for 10 minutes each at the 85° C. The solid was then collected by filtration and washed with a 10 wt % TiCl$_4$/toluene solution (265 ml) with agitation at 85° C., followed by addition of NPDE1 (2.0 g) in toluene (5.0 g) with heating at 85° C. for 60 minute, and followed by filtration. After filtration, the solid was again washed with the TiCl$_4$/toluene solution and NPDE1 (0.5 g) in toluene (2 g), but this time at 95° C. After again filtering, the solid was collected, and washed with the TiCl$_4$/toluene solution at 110° C. under agitation. Finally, the solid was washed with hexane (200 ml) four times under agitation at 60-65° C., with the catalyst being discharged as a hexane slurry.

Figure 7:
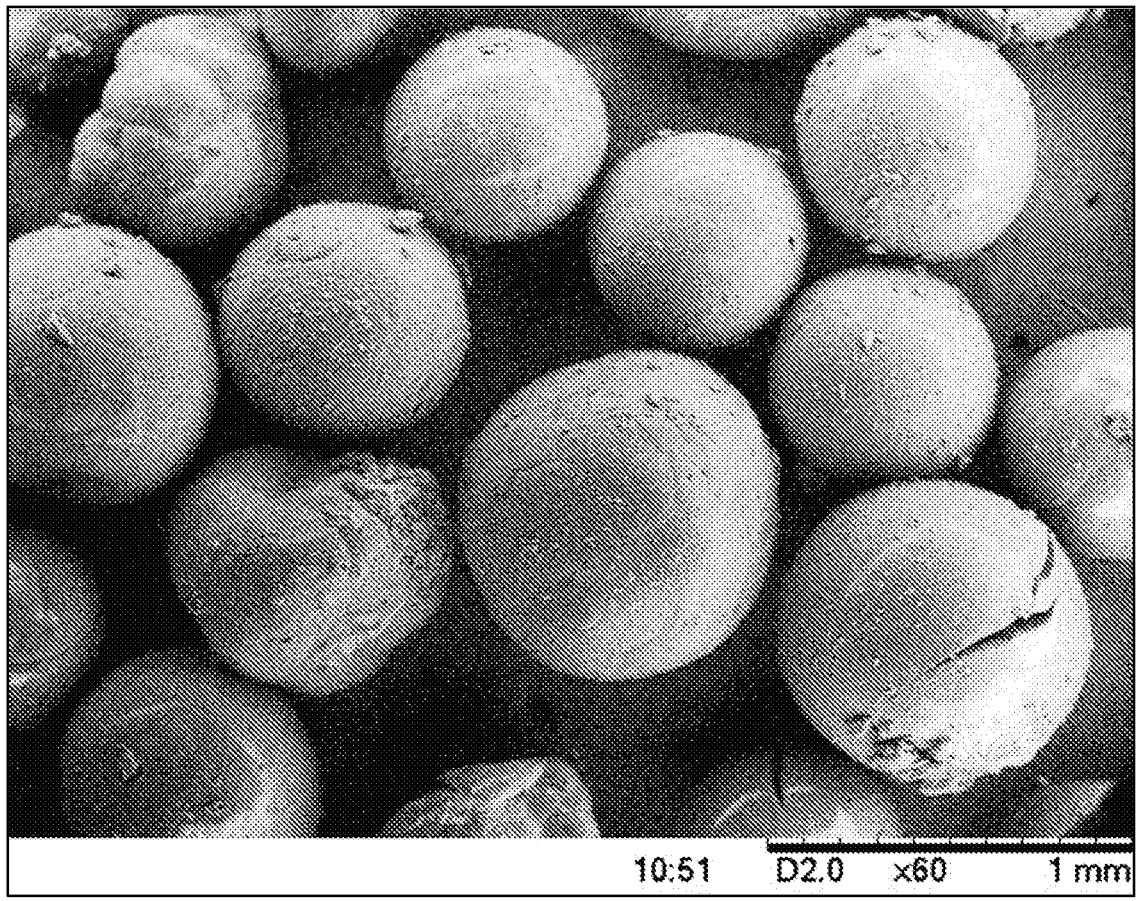
FIG. 7 shows a microscopic view of the polymer produced with the catalyst component of Example 34.

Example 34 demonstrates the preparation of a spherical catalyst component made using epoxy compounds to dissolve MgCl$_2$, but without the use of an anhydride. Instead, an organosilicon compound, Al(O-iPr)3, and ethyl benzoate were used. The polymer produced with this catalyst (FIG. 7) shows high density particles and good sphericity (microspheres).

Example 35

Demonstration of the preparation and performance of the spherical catalyst component using TEOS instead Syltherm. Example 34 was repeated, however the Syltherm was replaced with TEOS (5 g) and dibutyl ether (12 g) was used.

Example 36 (Comparative)

A catalyst was made with EB (no PDMS, no aluminum alkoxide) demonstrating irregular catalyst/polymer morphology, low BD of catalyst/polymer and broad catalyst/PP span. Example 33 was repeated, however no PDMS and Al(OCH(CH3)2)3 were added. Example 35 demonstrates the preparation of a catalyst component, prepared using an epoxy compound to dissolve MgCl$_2$, and ethyl benzoate. No organosilicon compounds and Al(O-iPr)3 were used. The polymer produced with the catalyst of Example 35, exhibits low bulk density particles and with an irregular morphology.

TABLE 11

Analytical Data for the spherical solid catalyst components and polymer properties

| | Example | | |
|---|---|---|---|
| | 34 | 35 | 36 (Comp.) |
| D10 (μ) | 12.6 | 16.9 | 8.6 |
| D50 (μ) | 20.7 | 27.2 | 28.8 |
| D90 (μ) | 34.7 | 44.2 | 60.2 |

TABLE 11-continued

Analytical Data for the spherical solid catalyst components and polymer properties

| | Example | | |
|---|---|---|---|
| | 34 | 35 | 36 (Comp.) |
| Span | 1.069 | 1.004 | 1.792 |
| Ti % | 1.77 | 2.31 | 2.65 |
| Mg % | 16.23 | 18.50 | 17.23 |
| NPDE1, % | 12.9 | 12.5 | 11.3 |
| CE kg/g | 66.4 | 58.6 | 67.1 |
| MFR, g/10 min | 0.12 | 0.73 | 0.22 |
| XS, % | 1.12 | 1.49 | 1.60 |
| BD, g/ml | 0.439 | 0.390 | 0.387 |
| PP D50 (μ) | 827 | 1098 | 957 |
| PP Span | 0.912 | 0.808 | 1.325 |

Because polymer morphology is a replica of the catalyst morphology, the same trends in the catalyst morphology are expected. The catalyst and polymer morphology are key factors to consider in any commercial polymer production process. It is known that some polymerization processes require good flowability of the polymer, or transfer of the polymer from one reactor unit to another.

The catalysts/methods lead to the production of poly-α-olefins having a a variable molecular weight distribution. Polydispersity Index (PI) is strictly connected with the molecular weight distribution of the polymer.

Examples 37-39 demonstrate properties of polypropylene (PI and rheological breadth) produced with catalyst components using different internal donors

TABLE 12

PI and phelogical breadth of PP produced with selected catalysts

| Example | Catalyst | Internal donor | PI | Rheological Breadth |
|---|---|---|---|---|
| Example 37 | Catalyst based on example 8 | NPDE1 | 5.2559 | 0.2754 |
| Example 38 | Catalyst based on example 8 | NPDE1 | 6.1586 | 0.2892 |
| Example 39 | Catalyst based on example 31 | DEMH | 3.8113 | 0.3912 |

Example 40-43

The solid catalyst component from example 11 was used for bulk propylene polymerization as described above except a mixture of external donors sold under the designation D6500 were used, which are commercially available from W.R. Grace and Company. The table below demonstrates effect of amount of a mixture of external donors on XS level (catalyst activity) and polymer properties.

TABLE 13

| Example | Catalyst Component | Donor (ml) | Corr CE kg/g | B/D | MFR, g/10 min | XS, % | PP D50, microns | Span | b/l3 |
|---|---|---|---|---|---|---|---|---|---|
| Example 40 | Example 15 | 0.39 | 108.8 | 0.411 | 2.46 | 5.53 | 1698 | 1.042 | 0.596 |
| Example 41 | Example 15 | 0.78 | 96.8 | 0.439 | 0.73 | 3.27 | 716 | 1.094 | 0.695 |
| Example 42 | Example 15 | 1.17 | 85.6 | 0.446 | 0.91 | 2.25 | 562 | 0.859 | 0.751 |
| Example 43 | Example 15 | 1.56 | 91.6 | 0.429 | 1.25 | 1.99 | 563 | 0.917 | 0.751 |

The solid catalyst components or the solid precipitates can be used for ethylene polymerization process. Example 44 demonstrates catalyst activity and polyethylene properties produced with solid precipitate from example 15. The polymerization was conducted in hexane in a one-gallon reactor. The reactor was purged at 100° C. under nitrogen for one hour. At room temperature, 0.6 ml of 25-wt % triethylaluminum (TEA1) in heptane was added into the reactor. Then 1500 ml of hexane was added and 10 mg of the catalyst prepared above were added into the reactor. The reactor was pressurized with H2 to 60.0 psig then charged with ethylene to 116 psig. The reactor was heated to and held at 80° C. for two hours. At the end of the hold, the reactor was vented and the polymer was recovered.

bottle. Agitate at 60 C/600 rpm/8 hr+. Cool down to 25 C. Leave for next day under N2 Blanket. Add 27 g toluene, 1.12 g ethyl benzoate in 3 g toluene, 0.75 g TEOS in 3 g toluene @ 25 C. Cool to −25 C @ 600 rpm and add 65.2 g TiCl4 slowly. Raise from −25 C to 35 C over 30 min @ 300 rpm. Hold at 35 C for 30 min/300 rpm. Raise from 35 C to 85 C in 30 min and hold at 85 C for 30 min @ 300 rpm. Wash with 50 ml toluene 3× at 400 rpm for 10 min @80 C JT. Filter. Next day. Add 65 ml 10% TiCl4/toluene to rx/400 rpm. Add (0.25 g NPDE in 2 g toluene) at 70 C. Heat to 85c. Hold and agitate at 85 C/1 hr/400 rpm. Filter. Act1=65 ml 10% TiCl4/tol and (0.5 g NPDE in 2 g toluene @70 C). Hold at 95 C/1 hr; Act2=65 ml 10% TiCl4/tol at 110 C/30 min; Act3=65 ml 10% TiCl4/tol at 110 C/30 min; Act4=65 ml

TABLE 14

Ethylene polymerization with the solid component

| Example | D50 | Ti, % | Mg, % | CE, kg/g | BD, g/cm³ | MFI2 | MFI10 | MFI22 | MFI Ratio | PE D50 | Span |
|---|---|---|---|---|---|---|---|---|---|---|---|
| Example 44 | 12 | 4.45 | 15.84 | 35.2 | 0.303 | 1.918 | 17.205 | 72.484 | 37.791 | 330 | 0.883 |

Examples 45 and 46 demonstrate the improved lifetime of catalysts made in accordance with the present disclosure.

The lifetime of polymerization catalysts can be important for the commercial production of polyolefins. The long lifetime of the catalyst allows to conduct polymerization processes continually in different reactors producing homopolymers and co-polymers with a variety of properties. Many Ziegler-Natta catalysts, in particular non-phthalate donor catalysts, have a limited lifetime. Usually the catalyst activity for these types of catalysts is very high at the beginning of the polymerization process and decreases dramatically thereafter. In two or three reactor polymerization processes, these catalysts are not useful due to low catalyst activity after the first reactor polymerization. The decay of the catalyst activity is related to deactivation of active centers on the catalyst surface.

10% TiCl4/tol at 110 C/30 min; wash with 50 ml hexane/400 rpm at 65 C JT/agitate 5 min(4×); discharge as hexane slurry.

The above catalysts were then used to produce polypropylene polymers.

A reactor was baked at 100° C. under nitrogen flow for 30 minutes prior to the polymerization run. The reactor was cooled to 30-35° C. and cocatalyst (1.5 ml of 25 wt % triethylaluminum (TEA1)), C-donor [cyclohexylmethydimethoxysilane] (1 ml), hydrogen (3.5 psi) and liquid propylene (1500 ml) were added in this sequence into the reactor. The catalyst (5-10 mg), loaded as a mineral oil slurry, was pushed into the reactors using high pressure nitrogen. The polymerization was performed for one or two hours at 70° C. After the polymerization, the reactors were cooled to 22° C., vented to atmospheric pressure, and the polymer collected.

The following results were obtained:

| Example No. | Run time | CE kg/g | B/D g/cm³ | MFR g/10 min | XS (%) | D-50 (Microns) | Span | b/l3 | Split 1st & 2nd hs (%) |
|---|---|---|---|---|---|---|---|---|---|
| 45 | 60 | 69.3 | 0.444 | 0.24 | 1.36 | 793 | 0.839 | 0.815 | 55.4 |
| 45 | 120 | 125.2 | 0.447 | 0.49 | 1.84 | 1009 | 0.816 | 0.822 | 44.6 |
| 46 | 60 | 82.2 | 0.417 | 0.18 | 2.21 | 824 | 0.501 | 0.720 | 55.4 |
| 46 | 120 | 148.3 | 0.416 | 0.62 | 2.53 | 1018 | 0.474 | 0.723 | 44.6 |

Catalyst systems made in accordance with the present disclosure were tested for catalyst lifetime. In particular, the kinetics of the catalysts were evaluated after 1 hour (45 minutes) and after 2 hours (105 minutes) to determine the difference in catalyst activity over the entire period of time.

The following catalysts were prepared.

Example No. 45

The catalyst was prepared as described in Example No. 34.

Example No. 46

Add 3.3 g TOHO MgCl2, 0.125 g Al(O-iPr)3, 3.55 g ECH, 9.1 g TBP, 15 g toluene, 0.75 g Syltherm in serum As shown above, the catalysts made according to the present disclosure have excellent catalyst activity during the entire two hour period of polymerization. More particularly, the data illustrates that catalyst systems in accordance with the present disclosure have an extended lifetime such that the catalyst activity during a second hour of polymerization is not less than about 8%, such as not less than about 7% of the catalyst activity of the catalyst system during a first hour of polymerization.

Examples 47-51

The following examples were conducted in order to demonstrate the dramatic and unexpected improvement in the flowability or polymers made according to the present disclosure. In particular, the following examples demonstrate the improved flowability properties of elastomeric propylene-ethylene copolymers made in accordance with the present disclosure that contain relatively high amounts of amorphous polyethylene that provide the polymers with elastomeric properties. The examples below, for instance, had a rubber content of greater than 30% by weight. Such polymer resins typically have very poor flow properties and have a tendency to stick together and form agglomerates.

The propylene-ethylene random copolymers were formed using a gas phase polymerization process. The reactor set up included two fluidized bed reactors in series. Polypropylene homopolymer was produced in the first reactor. Non-phthalate catalysts were used to produce the polymers. Example numbers 47 and 48 below are comparative examples. In these examples, a commercially available catalyst sold under the name CONSISTA and available from the W.R. Grace & Co. was used. In Example numbers 49-51, however, a catalyst was made in accordance with Example No. 8 above except a scale of 20 kg was used.

In the first reactor, the catalyst was used in conjunction with triethylaluminum as a cocatalyst. A mixed external electron donor was also used. In Examples 47 and 48, the mixed external electron donors included dicyclopentyldimethoxysilane (DCPDMS) as the selectivity control agent and iso-propylmyristate (IPM) as the activity limiting agent. In Example numbers 49-51, the mixed external election donors included n-propyltrimethoxysilane (NPTMS) as the selectivity control agent and pentyl valerate (PV) as the activity limiting agent.

The homopolymer powder produced in the first reactor was passed to the second reactor where the gas phase contained ethylene and propylene. The powder was held in the second reactor for a residence time long enough to produce a powder with an ethylene/propylene rubber content of approximately 31 weight %.

The reactor set up was a two gas phase fluidized-bed UNIPOL reactor system available for license by W.R. Grace & Co. and is described in U.S. Pat. No. 4,882,380, which is incorporated herein by reference.

After the propylene-ethylene copolymers were produced, the polymer resins were tested according to the Cup Test as described above. The following Table includes operating conditions, product information, and the Cup Test results.

|  | Example 47 | Example 48 | Example 49 | Example 50 | Example 51 |
| --- | --- | --- | --- | --- | --- |
| Rx1 Donor Composition | 80/20 IPM/DCPDMS | 80/20 IPM/DCPDMS | 90/10 PV/NPTMS | 90/10 PV/NPTMS | 90/10 PV/NPTMS |
| Rx2 Antifoulant Composition | 60/40 IPM/NPTMS | 60/40 IPM/NPTMS | 60/40 IPM/NPTMS | 60/40 IPM/NPTMS | 60/40 IPM/NPTMS |
| Rx1 MF (g/10 min) | 29.5 | 44.2 | 63.7 | 64.2 | 63.8 |
| Rx1 XS Wet (wt %) | 1.78 | 1.73 | 1.71 | 1.66 | 1.62 |
| Rx1 Productivity-XRF (lb/lb) | 60870 | 56757 | 25577 | 27143 | 27708 |
| Rx1 Temp (° C.) | 71.9 | 72.1 | 72.0 | 72.0 | 72.0 |
| Rx1 C3PP (psia) | 319.9 | 320.0 | 318.7 | 319.5 | 319.7 |
| Rx1 Bed Wt (lb) | 50.5 | 53.0 | 50.9 | 48.9 | 49.2 |
| Rx1 FBD (lb/ft3) | 8.0 | 8.2 | 7.3 | 7.2 | 7.2 |
| Rx1 SBD (lb/ft3) | 20.5 | 22.5 | 18.4 | 17.9 | 17.9 |
| Rx1 APS (inch) | 0.0167 | 0.0166 | 0.0175 | 0.0172 | 0.0209 |
| Rx1 Fines (wt %) | 9.1 | 11.0 | 6.2 | 7.3 | 4.1 |
| Rx1 Al (ppmw) | 26 | 22 | 25 | 26 | 28 |
| Rx1 Ti (ppmw) | 0.69 | 0.74 | 1.04 | 0.98 | 0.96 |
| GRADEX Rx1 10 Mesh (wt %) | 0.00 | 0.00 | 0.00 | NT | 0.09 |
| GRADEX Rx1 18 Mesh (wt %) | 3.29 | 3.92 | 0.63 | NT | 2.82 |
| GRADEX Rx1 35 Mesh (wt %) | 26.73 | 26.32 | 36.25 | NT | 49.44 |
| GRADEX Rx1 60 Mesh (wt %) | 43.25 | 40.72 | 41.48 | NT | 33.27 |
| GRADEX Rx1 120 Mesh (wt %) | 17.58 | 18.08 | 15.47 | NT | 10.24 |
| GRADEX Rx1 200 Mesh (wt %) | 5.42 | 5.52 | 4.61 | NT | 2.82 |
| GRADEX Rx1 Pan (wt %) | 3.73 | 5.44 | 1.56 | NT | 1.32 |

|  | Example 47 | Example 48 | Example 49 | Example 50 | Example 51 |
|---|---|---|---|---|---|
| Rx1 SCA in resin ppm | 86 | 74 | 48 | 109 | 97 |
| Rx2 MF (g/10 min) | 18.93 | 28.66 | 22.27 | 22.33 | 21.07 |
| Rx2 Temp (° C.) | 65 | 65 | 70 | 70 | 70 |
| Rx2 C3 PP (psi) | 182.0 | 167.9 | 137.5 | 119.0 | 121.3 |
| SCA2/SCA1 | 0.44 | 0.38 | 0.15 | 0.15 | 0.15 |
| Rx2 Bed Wt (lb) | 87 | 91 | 83 | 84 | 85 |
| Rx2 FBD (lb/ft3) | 12.87 | 13.02 | 11.92 | 12.45 | 12.53 |
| Rx2 SBD (lb/ft3) | 17.9 | 18.4 | 16.7 | 16.7 | 15.6 |
| Rx2 APS (inch) | 0.046 | 0.044 | 0.038 | 0.034 | 0.036 |
| Rx2 Fines (wt %) | 0.08 | 0.09 | 0.22 | 0.40 | 0.40 |
| Rx2 Ti (ppmw) | 0.45 | 0.38 | 0.73 | 0.77 | 0.81 |
| Rx2 Al (ppmw) | 21 | 19 | 34 | 26 | 28 |
| Rx2 10 Mesh (wt %) | 5.52 | 4.19 | 2.01 | NT | 2.92 |
| Rx2 18 Mesh (wt %) | 50.53 | 49.77 | 36.06 | NT | 29.08 |
| Rx2 35 Mesh (wt %) | 38.77 | 38.05 | 52.34 | NT | 50.73 |
| Rx2 60 Mesh (wt %) | 5.11 | 7.81 | 9.07 | NT | 16.20 |
| Rx2 120 Mesh (wt %) | 0.00 | 0.09 | 0.30 | NT | 0.66 |
| Rx2 200 Mesh (wt %) | 0.08 | 0.00 | 0.22 | NT | 0.27 |
| Rx2 Pan (wt %) | 0.00 | 0.09 | 0.00 | NT | 0.13 |
| Fc (wt %) | 33.2 | 31.0 | 34.6 | 31.8 | 31.3 |
| Ec (wt %) | 41.1 | 41.7 | 41.9 | 39.8 | 40.2 |
| Et (wt %) | 13.6 | 12.9 | 14.5 | 12.7 | 12.6 |
| 30 Minute Cup Test Score (seconds) | 42 | 34 | 9 | 7 | 8 |

As shown above, propylene-ethylene copolymers made in accordance with the present disclosure had dramatically reduced Cup Test Times in contrast to the comparative examples.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A polymer composition comprising propylene-ethylene copolymer particles including propylene as a primary monomer, the propylene-ethylene copolymer particles comprising ethylene in an amount greater than 3% by weight, the propylene-ethylene copolymer exhibiting a melt flow rate according to ASTM D1238 at 230° C. and a weight of 2.16 kg, of about 50 g/10 min to about 500 g/10 min, and wherein the propylene-ethylene copolymer particles exhibit a Cup Test Index of 2 or less.

2. The polymer composition of claim 1, wherein the propylene-ethylene copolymer contains ethylene in an amount greater than about 8% by weight.

3. The polymer composition of claim 1, wherein the propylene-ethylene copolymer contains ethylene in an amount greater than about 10% by weight.

4. The polymer composition of claim 1, wherein the propylene-ethylene copolymer particles exhibit a Cup Test time of less than 10 seconds.

5. The polymer composition of claim 1, wherein the propylene-ethylene copolymer includes a first polymer phase combined with a second polymer phase comprising an elastomeric propylene-ethylene copolymer.

6. The polymer composition of claim 1, wherein the propylene-ethylene copolymer particles have a D50 particle size of from about 300 microns to about 3000 microns and have a bulk density of from about 0.4 g/cm$^3$ to about 0.6 g/cm$^3$.

7. The polymer composition of claim 1, wherein the propylene-ethylene copolymer is produced in the presence of a catalyst system, the catalyst system comprising a solid catalyst component combined with an aluminum compound, at least one selectivity control agent, and optionally an activity limiting agent, the solid catalyst component comprising a reaction product of a magnesium compound with an epoxy compound, the solid catalyst component further comprising an organic phosphorus compound, a titanium compound, an organosilicon compound, and an internal electron donor.

8. The polymer composition of claim 1, wherein the propylene-ethylene copolymer is produced in the presence of a catalyst system comprising a solid catalyst component combined with an aluminum compound, at least one selectively control agent, and optionally an activity limiting agent, the solid catalyst component comprising:

magnesium compound including a halide-containing magnesium compound and a reaction product of a magnesium compound with an epoxy compound;

an organic phosphorus compound;

a titanium compound;

an organosilicon compound;

an internal electron donor, the internal electron donor comprising an aryl diester, a diether, a succinate, an organic acid ester, a polycarboxylic acid ester, a polyhydroxy ester, a heterocyclic polycarboxylic acid ester, an inorganic acid ester, an alicyclic polycarboxylic acid ester, a hydroxy-substituted carboxylic acid ester compound having 2 to 30 carbon atoms, or a compound having at least one ether group and at least one ketone group, or mixtures thereof;

wherein the solid catalyst component is free of side reaction products between a carboxylic acid or an anhydride thereof and a magnesium compound or a titanium compound.

9. The polymer composition of claim 1, wherein the propylene-ethylene copolymer is produced in the presence of a catalyst system that has an extended lifetime such that a catalyst activity of the catalyst system during a second hour of polymerization is no less than about 8% of a catalyst activity of the catalyst system during a first hour of polymerization.

10. A polymer composition comprising particles of polypropylene homopolymer, polypropylene copolymer, or a mixture thereof, wherein the particles have a D50 particle size of about 150 microns to about 3000 microns, the particles exhibit an aspect ratio, B/L3, of greater than about 0.6, and wherein the polymer composition exhibits a bulk density of greater than 0.415 g/cm$^3$; wherein the polypropylene homopolymer or polypropylene copolymer exhibits a melt flow rate according to ASTM D1238 at 230° C. and a weight of 2.16 kg from 50 g/10 min to 500 g/10 min; and wherein the particles comprise microspheres.

11. The polymer composition of claim 10, wherein the particles have a B/L3 of from about 0.7 to about 1.0.

12. The polymer composition of claim 10, wherein the polymer composition has a bulk density of from 0.42 g/cm$^3$ to 0.60 g/cm$^3$.

13. The polymer composition of claim 10, wherein the polypropylene polymer is produced in the presence of a catalyst system, the catalyst system comprising a solid catalyst component combined with an aluminum compound, at least one selectivity control agent, and optionally an activity limiting agent, the solid catalyst component comprising a reaction product of a magnesium compound with an epoxy compound, the solid catalyst component further comprising an organic phosphorus compound, a titanium compound, an organosilicon compound, and an internal electron donor.

14. The polymer composition of claim 13, wherein the solid catalyst component further comprises a supportive donor, the supportive donor comprising a mono aryl ester, the internal electron donor is represented by one of the following formulas:

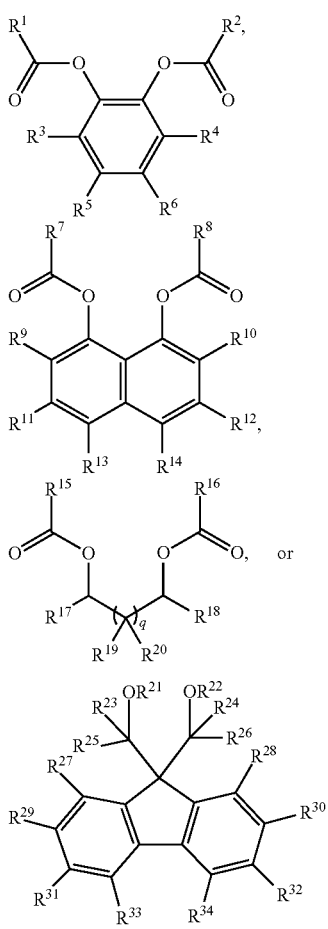

wherein:
each of $R^1$ through $R^{34}$ is independently H, F, Cl, Br, I, alkyl, cycloalkyl, cycloalkylalkyl, aryl, aralkyl, heterocyclyl, heterocyclylalkyl, heteroaryl, or heteroarylalkyl; and q is an integer from 0 to 12.

15. The polymer composition of claim 10, wherein the polypropylene polymer comprises a polypropylene homopolymer.

16. The polymer composition of claim 10, wherein the polypropylene polymer comprises a propylene-ethylene copolymer.

17. The polymer composition of claim 16, wherein the polypropylene polymer comprises a heterophasic random copolymer.

18. The polymer composition of claim 10, wherein the polypropylene polymer is produced in the presence of a catalyst system, the catalyst system comprising a solid catalyst component combined with an aluminum compound, at least one selectively control agent, and optionally an activity limiting agent, the solid catalyst component comprising:
magnesium compound including a halide-containing magnesium compound and a reaction product of a magnesium compound with an epoxy compound;
an organic phosphorus compound;
a titanium compound;
an organosilicon compound;
an internal electron donor, the internal electron donor comprising an aryl diester, a diether, a succinate, an organic acid ester, a polycarboxylic acid ester, a polyhydroxy ester, a heterocyclic polycarboxylic acid ester, an inorganic acid ester, an alicyclic polycarboxylic acid ester, a hydroxy-substituted carboxylic acid ester compound having 2 to 30 carbon atoms, or a compound having at least one ether group and at least one ketone group, or mixtures thereof; wherein the solid catalyst component is free of side reaction products between a carboxylic acid or an anhydride thereof and a magnesium compound or a titanium compound.

* * * * *